(12) United States Patent
Ikeda et al.

(10) Patent No.: US 7,858,313 B2
(45) Date of Patent: Dec. 28, 2010

(54) METHOD OF EVALUATING DRUG SENSITIVITY BY ANALYZING GIRK CHANNEL GENES

(75) Inventors: Kazutaka Ikeda, Tokyo (JP); Masakazu Hayashida, Tokyo (JP); Daisuke Nishizawa, Tokyo (JP); Ichiro Sora, Sendai (JP)

(73) Assignee: Tokyo Metropolitan Organization for Medical Research, Tokyo (JP)

( * ) Notice: Subject to any disclaimer, the term of this patent is extended or adjusted under 35 U.S.C. 154(b) by 424 days.

(21) Appl. No.: 11/896,256

(22) Filed: Aug. 30, 2007

(65) Prior Publication Data
US 2009/0092972 A1 Apr. 9, 2009

(30) Foreign Application Priority Data
Aug. 31, 2006 (JP) ............................ P2006-235352
Aug. 28, 2007 (JP) ............................ P2007-221298

(51) Int. Cl.
*C12Q 1/68* (2006.01)
*C07H 21/02* (2006.01)
*C07H 21/04* (2006.01)

(52) U.S. Cl. ........................ 435/6; 536/23.1; 536/23.5; 536/24.1

(58) Field of Classification Search ........................ None
See application file for complete search history.

(56) References Cited

U.S. PATENT DOCUMENTS

| | | | | |
|---|---|---|---|---|
| 2004/0214324 | A1* | 10/2004 | Isacson et al. | 435/368 |
| 2005/0287574 | A1* | 12/2005 | Soykan et al. | 435/6 |
| 2007/0258898 | A1* | 11/2007 | Ballinger et al. | 424/9.1 |
| 2008/0248470 | A1* | 10/2008 | Kim et al. | 435/6 |

OTHER PUBLICATIONS

Halushka et all. Nature. Jul. 1999. 22: 239-247.*
Hirschhorn et al. Genetics in Medicine. 2002. 4(2): 45-61.*
Suzuki et al. Eur Arch Psychiatry Clin Neurosci (2001). 251: 57-59.*
NCBI SNP Database, National Center for Biotechnology Information, National Library of Medicine, NIH (Bethesda, MD, USA) rs2070995, GenBank Accession S78684, Jul. 9, 2001.*
Tanizawa et al., "A human pancreatic islet inwardly rectifying potassium channel: cDNA cloning, determination of the genomic structure and genetic variations in Japanese NIDDM patients," Diabetologia (1996) vol. 39, pp. 447-452.
Penn et al., "Single exon nucleic acid probes for analyzing gene expression in human hearts," XP-002463412, Database accession No. ABA25297, Jan. 23, 2002.
"NEDO human cDNA sequencing project," XP-002463413, Database accession No. DB310545, Feb. 27, 2006.
Blednov et al., "A pervasive mechanism for analgesia: Activation of GIRK2 channels," Proceedings of the National Academy of Sciences of USA, Jan. 7, 2003, vol. 100, No. 1, pp. 277-282, XP-002328189.
Marker et al., "Hyperalgesia and blunted morphine analgesia in G protein-gated potassium channel subunit knockout mice," Neuroreport, vol. 13, No. 18, p. 2509-2513, Dec. 20, 2002, XP-002971124.
Marker et al., "Spinal G-Protein-Gated K+ Channels Formed by GIRK1 and GIRK2 Subunits Modulate Thermal Nociception and Contribute to Morphine Analgesia," The Journal of Neuroscience, Mar. 17, 2004, vol. 24, No. 11, pp. 2806-2812, XP-002463411.
Ocana et al., "Potassium channels and pain: present realities and future opportunities," European Journal of Pharmacology, vol. 500, (2004), pp. 203-219.
Sakura et al., "Characterization and variation of a human inwardly-rectifying K-channel gene (KCNJ6): a putative ATP-sensitive K-channel subunit," FEBS Letters, vol. 367 (1995) pp. 193-197, XP-002298421.
Hallmann et al., "Mutation Analysis of the Inwardly Rectifying K+ Channels KCNJ6 (GIRK2) and KCNJ3 (GIRK1) in Juvenile Myoclonic Epilepsy," American Journal of Medical Genetics (Neuropsychiatric Genetics) vol. 96, pp. 8-11, (2000) XP-002298426.
Vaughn et al., "Genomic Structure and Expression of Human KCNJ9 (Kir3.3/GIRK3)," Biochemical and Biophysical Research Communications, vol. 274, pp. 302-309, (2000) XP-002324142.
Kazutaka Ikeda et al., "Involvement of G-Protein-Activated Inwardly Rectifying $K^+$ (GIRK) Channels in Opioid-Induced Analgesia," Neuroscience Research vol. 38, pp. 113-116 (2000).
Toru Kobayashi et al., "Ethanol Opens G-Protein-Activated Inwardly Rectifying $K^+$ Channels," nature neuroscience, vol. 2, No. 12, pp. 1091-1097 (Dec. 1999).
Kazutaka Ikeda et al., "Molecular Mechanisms of Analgesia Induced by Opioids and Ethanol: Is the GIRK Channel One of the Keys?," Neuroscience Research, vol. 44, 121-131 (2002).
Toru Kobayashi et al., "G Protein-Activated Inwardly Rectifying Potassium Channels as Potential Therapeutic Targets," Current Pharmaceutical Design, vol. 12, 4513-4523 (2006).
Kazutaka Ikeda et al., "How Individual Sensitivity to Opiates Can Be Predicted by Gene Analyses," TRENDS in Pharmacological Sciences, vol. 26, No. 6, pp. 311-317 (Jun. 2005).

* cited by examiner

*Primary Examiner*—Carla Myers
(74) *Attorney, Agent, or Firm*—Birch, Stewart, Kolasch & Birch, LLP

(57) ABSTRACT

A method of evaluating drug sensitivity or disease vulnerability, includes linking a gene polymorphism in a GIRK channel gene or a haplotype comprising the gene polymorphism to individual drug sensitivity or individual disease vulnerability.

15 Claims, 3 Drawing Sheets

```
                         SEQUENCE LISTING

<160> NUMBER OF SEQ ID NOS: 25

<210> SEQ ID NO 1
<211> LENGTH: 101
<212> TYPE: DNA
<213> ORGANISM: Homo Sapiens

<400> SEQUENCE: 1
tatgactcag aagtaatagc aagtcagatt acaacctctt agggaaaatc racagcaaat      60
acaagctcac aggccgtgtg tacggttgac ttttacatga c                        101

<210> SEQ ID NO 2
<211> LENGTH: 101
<212> TYPE: DNA
<213> ORGANISM: Homo Sapiens

<400> SEQUENCE: 2
aattgacaca acacctctc catattacag tcattttag agggcagaca rcattcttga       60
ggggacctga attgctaggt aattaaaatg tatgtatgta g                        101

<210> SEQ ID NO 3
<211> LENGTH: 101
<212> TYPE: DNA
<213> ORGANISM: Homo Sapiens

<400> SEQUENCE: 3
```

```
agattccccc agcatggagc acccacgttt ccagtggcgg gggatgcacg ytggtttgtg    60
cccagcccgc ccccaccaag cccggtcctc gacgcgctga c                        101
```

<210> SEQ ID NO 4
<211> LENGTH: 101
<212> TYPE: DNA
<213> ORGANISM: Homo Sapiens

<400> SEQUENCE: 4

```
agcacccacg tttccagtgg cgggggatgc acgttggttt gtgcccagcc ygcccccacc    60
aagcccggtc ctcgacgcgc tgacacgcta gctggcatgg g                        101
```

<210> SEQ ID NO 5
<211> LENGTH: 101
<212> TYPE: DNA
<213> ORGANISM: Homo Sapiens

<400> SEQUENCE: 5

```
cccggaccgc gccggcgctg tgcggctttt tccccagcac gcggcgctgc rctcgctttt    60
atctcggagc cgcgtcgctt cgtgcgctgc cagcggggct c                        101
```

<210> SEQ ID NO 6
<211> LENGTH: 101
<212> TYPE: DNA
<213> ORGANISM: Homo Sapiens

<400> SEQUENCE: 6

```
agatcaattc atatctaaga catgttttac agataattgt cttttcttct yacctccagg    60
aaaagcacaa agaagaaact gcaacaatgg ccaagctgac a                        101
```

<210> SEQ ID NO 7
<211> LENGTH: 101
<212> TYPE: DNA
<213> ORGANISM: Homo Sapiens

<400> SEQUENCE: 7

```
acagaaacca ccattggtta tggctaccgg gtcatcacag ataaatgccc rgagggaatt    60
attcttctct taatccaatc tgtgttgggg tccattgtca a                        101
```

<210> SEQ ID NO 8
<211> LENGTH: 101
<212> TYPE: DNA
<213> ORGANISM: Homo Sapiens

<400> SEQUENCE: 8

```
agtgagatcc tgtggggtta ccggttcaca cctgtcctga ccctggagga ygggttctac    60
gaagttgact acaacagctt ccatgagacc tatgagacca g                        101
```

<210> SEQ ID NO 9
<211> LENGTH: 101
<212> TYPE: DNA
<213> ORGANISM: Homo Sapiens

<400> SEQUENCE: 9

```
atgaatccaa agtttagtgc cctagctggg caaacccttc tcttctcccc scaacacaat    60 cttccttgt ctctcattct cttctttttt ctgtctctct t                         101
```

<210> SEQ ID NO 10

```
<211> LENGTH: 101
<212> TYPE: DNA
<213> ORGANISM: Homo Sapiens

<400> SEQUENCE: 10
ttatatattt gtccaaaccc acagagtgta caacaccaaa agtgaaccct matgtcagct      60
atggactttg ggcgattatg atgtcaatgt agcttcatca c                         101

<210> SEQ ID NO 11
<211> LENGTH: 101
<212> TYPE: DNA
<213> ORGANISM: Homo Sapiens

<400> SEQUENCE: 11
taacacctgt cttatagagt tgccatgggg atgacatgag gcatgtgtct sgttcatatc      60
ccatgctcag tgaattagta gcagcagcca ctgtgtgttt g                         101

<210> SEQ ID NO 12
<211> LENGTH: 101
<212> TYPE: DNA
<213> ORGANISM: Homo Sapiens

<400> SEQUENCE: 12
ttatagagtt gccatgggga tgacatgagg catgtgtctc gttcatatcc satgctcagt      60
gaattagtag cagcagccac tgtgtgtttg tgtgtcttta t                         101

<210> SEQ ID NO 13
<211> LENGTH: 101
<212> TYPE: DNA
<213> ORGANISM: Homo Sapiens

<400> SEQUENCE: 13
ttccttctag ctaccgcctt ctggatccat ggcctctcca aaactagacc rtgatggtca      60
gcctgacctg agagcagcac ctgcacgcag agacccatgt t                         101

<210> SEQ ID NO 14
<211> LENGTH: 101
<212> TYPE: DNA
<213> ORGANISM: Homo Sapiens

<400> SEQUENCE: 14
gtgctgactc tggaggacgg cttctacgaa gtggactatg ccagctttca ygagactttt      60
gaggtgccca caccttcgtg cagtgctcga gagctggcag a                         101

<210> SEQ ID NO 15
<211> LENGTH: 101
<212> TYPE: DNA
<213> ORGANISM: Homo Sapiens

<400> SEQUENCE: 15
ctactggtcc atccccagcc ggctggatga gaaggtggag gaggagggggg yggggagggg    60 ggcgggtggg gaagctgggg ctgacaagga gcagaatggc t                         101

<210> SEQ ID NO 16
<211> LENGTH: 101
<212> TYPE: DNA
<213> ORGANISM: Homo Sapiens

<400> SEQUENCE: 16
tggtagcaga taaagacagc tgacagatac atagatggac cagtagacaa ytggtccact     60
```

```
cagggctgcc actaacctgt agaacacccc tgtgcaaatt t                          101

<210> SEQ ID NO 17
<211> LENGTH: 101
<212> TYPE: DNA
<213> ORGANISM: Homo Sapiens

<400> SEQUENCE: 17
ggaccagtag acaactggtc cactcagggc tgccactaac ctgtagaaca yccctgtgca     60
aattttaaaa aggaacccctt ttcctccaga cagatacagc c                        101

<210> SEQ ID NO 18
<211> LENGTH: 101
<212> TYPE: DNA
<213> ORGANISM: Homo Sapiens

<400> SEQUENCE: 18
ggcacatgag gagggtgccc tcctagctcc accctcacca ggatgaaggc rtgcaagggg     60
ctcagcaagg tgtgaatgac cttagtccgc aagttcaggg a                         101

<210> SEQ ID NO 19
<211> LENGTH: 101
<212> TYPE: DNA
<213> ORGANISM: Homo Sapiens

<400> SEQUENCE: 19
catgtggagt ggacattcaa aaacctggtt cctgtcctca aaataagggg yacctgggaa     60
aacagaggaa tctacctgtg gtgactgaac gagggataat t                         101

<210> SEQ ID NO 20
<211> LENGTH: 24
<212> TYPE: DNA
<213> ORGANISM: Artificial Sequence
<220> FEATURE:
<223> OTHER INFORMATION: Artificially synthesized oligonucleotide
      sequence

<400> SEQUENCE: 20
caggcattgt ggagcacgta ttac                                            24

<210> SEQ ID NO 21
<211> LENGTH: 24
<212> TYPE: DNA
<213> ORGANISM: Artificial Sequence
<220> FEATURE:
<223> OTHER INFORMATION: Artificially synthesized oligonucleotide
      sequence

<400> SEQUENCE: 21
caccccctct ttttcttatg gtca                                            24

<210> SEQ ID NO 22
<211> LENGTH: 60
<212> TYPE: DNA
<213> ORGANISM: Artificial Sequence
<220> FEATURE:
<223> OTHER INFORMATION: Artificially synthesized oligonucleotide
      sequence

<400> SEQUENCE: 22
ttctcaatag agacagaaac caccattggt tatggctacc gggtcatcac agataaatgt     60
```

-continued

```
<210> SEQ ID NO 23
<211> LENGTH: 23
<212> TYPE: DNA
<213> ORGANISM: Artificial Sequence
<220> FEATURE:
<223> OTHER INFORMATION: Artificially synthesized oligonucleotide
      sequence

<400> SEQUENCE: 23
gacaccagaa acagacggtc atc                                              23

<210> SEQ ID NO 24
<211> LENGTH: 25
<212> TYPE: DNA
<213> ORGANISM: Artificial Sequence
<220> FEATURE:
<223> OTHER INFORMATION: Artificially synthesized oligonucleotide
      sequence

<400> SEQUENCE: 24
ttggggcaaa tggagaagac acgag                                            25

<210> SEQ ID NO 25
<211> LENGTH: 25
<212> TYPE: DNA
<213> ORGANISM: Artificial Sequence
<220> FEATURE:
<223> OTHER INFORMATION: Artificially synthesized oligonucleotide
      sequence

<400> SEQUENCE: 25
ggacccctcc cttccatact ggttt                                            25
```

METHOD OF EVALUATING DRUG SENSITIVITY BY ANALYZING GIRK CHANNEL GENES

BACKGROUND OF THE INVENTION

1. Field of the Invention

The present invention relates to a method of evaluating drug sensitivity by analyzing GIRK channel genes.

2. Description of the Related Art

Pain is a pathology which is most frequently observed in the medical field, and it is often the case that the pain accompanying a disease is serious for the patient rather than the disease itself. The pain sensation plays an important role in terms of a biological warning system, however, excessive pain significantly decreases QOL (quality of life) unless it is properly controlled. Recently, importance of pain control has been recognized, palliative care including pain therapy has remarkably progressed, and there is a tendency of increasing the frequency and amount of use of various analgesics.

Heretofore, pharmacological analyses using a *Xenopus* oocyte protein expression system and weaver mutant mice, it has been known that a G protein-activated inwardly rectifying potassium channel (hereinafter referred to as a GIRK channel) plays an extremely important role in the molecular mechanism of analgesia by morphine, an alcohol or the like (Ikeda, K. et al., Involvement of G-protein-activated inwardly rectifying K+ (GIRK) channels in opioid-induced analgesia, Neurosci. Res., (2000) 38: 111-114.; Kobayashi, T. et al., Ethanol opens G-protein-activated inwardly rectifying K+ channels, Nature Neurosci., (1999) 2: 1091-1097.; Ikeda, K. et al., Molecular mechanisms of analgesia induced by opioids and ethanol: is the GIRK channel one of the keys?, Neurosci. Res., (2002) 44: 121-131.; and Kobayashi, T. et al., G protein-activated inwardly rectifying potassium channels as potential therapeutic targets., Current Pharmaceutical Design in press.). Further, the genetic mechanism of sensitivity to morphine is becoming clear (Ikeda, K. et al., How individual sensitivity to opiates can be predicted by gene analyses., Trends Pharmacol. Sci., (2005) 26: 311-317.).

SUMMARY OF THE INVENTION

The present invention provides a method of predicting an individual difference in drug sensitivity or disease vulnerability, more specifically, drug sensitivity or disease vulnerability associated with the required number of administration of analgesics, total amount of analgesics, vulnerability to drug dependence, prolongation of stimulant-induced psychosis or the like using GIRK channel gene polymorphisms.

The present inventors paid attention to GIRK channel genes and made intensive studies based on past findings and clinical data. As a result, they identified several useful gene polymorphisms by analyzing a correlation between various GIRK channel gene polymorphisms and drug sensitivity or disease vulnerability to analgesics and stimulants. They also found a linkage disequilibrium among these identified gene polymorphisms and revealed a significant correlation with drug sensitivity or disease vulnerability.

To be more specific, they revealed that the required number of administration of analgesics and total amount of analgesics change when a specific GIRK channel gene polymorphism differs and that the frequency of a specific GIRK channel gene polymorphism differs between methamphetamine-dependent patients and healthy subjects, and thus, the present invention has been completed.

That is, the present invention is as follows:

<1> A method of evaluating drug sensitivity, which comprises linking a gene polymorphism in the GIRK channel genes or a haplotype comprising the gene polymorphism to individual drug sensitivity.

<2> The method as described in <1> above, which comprises the steps of:

(1) selecting a gene polymorphism in a linkage disequilibrium block by performing a linkage disequilibrium analysis and a haplotype analysis in healthy subjects;

(2) analyzing a linkage between a genotype of the gene polymorphism in a test subject and drug sensitivity; and (3) using the gene polymorphism significantly linked to the drug sensitivity in the test subject for evaluation of drug sensitivity.

<3> A method of evaluating disease vulnerability, which comprises linking a gene polymorphism in the GIRK channel genes or a haplotype comprising the gene polymorphism to individual disease vulnerability.

<4> The method as described in <3> above, which comprises the steps of:

(1) selecting a gene polymorphism in a linkage disequilibrium block by performing a linkage disequilibrium analysis and a haplotype analysis in healthy subjects;

(2) comparing a gene polymorphism frequency of the gene polymorphism in test subjects with a gene polymorphism frequency of the gene polymorphism in healthy subjects; and (3) using the gene polymorphism with a significant difference in the gene polymorphism frequency between the test subjects and the healthy subjects for evaluation of disease vulnerability.

<5> The method as described in <3> or <4> above, wherein the disease vulnerability is vulnerability to pain sensitivity or drug dependence.

<6> The method as described in any of <1> to <5> above, wherein the gene polymorphism is at least one gene polymorphism selected from the group consisting of single nucleotide polymorphisms, insertion polymorphisms, deletion polymorphisms and nucleotide repeat polymorphisms.

<7> The method as described in any of <1> to <6> above, wherein the gene polymorphism is at least one gene polymorphism selected from the group consisting of A-1361G, G-1250A, T-244C, C-227T, A-68G, IVS1C75167T, A1032G, C1569T and C1843G in the GIRK2 gene, and A-1329C, C-979G, C-968G, A-447G, C1211T, C1339T, C1781T, C1817T, G2069A and C2429T in the GIRK3 gene.

<8> The method as described in any of <1> to <7> above, wherein the haplotype is at least one haplotype selected from those shown in the following tables.

TABLE 1

| Gene name: GIRK2 Haplotype No. | Gene polymorphism name | | | | | | | | |
|---|---|---|---|---|---|---|---|---|---|
| | A-1361G | G-1250A | T-244C | C-227T | A-68G | IVS1 C75167T | A1032G | C1569T | C1843G |
| 1 | A | A | C | T | G | T | G | T | C |
| 2 | A | G | T | C | G | T | G | T | C |
| 3 | A | A | C | T | G | T | A | T | C |
| 4 | A | G | T | C | A | T | G | T | C |

TABLE 1-continued

| Gene name: GIRK2 Haplotype No. | Gene polymorphism name | | | | | | | | |
|---|---|---|---|---|---|---|---|---|---|
| | A-1361G | G-1250A | T-244C | C-227T | A-68G | IVS1 C75167T | A1032G | C1569T | C1843G |
| 5 | A | A | C | T | G | C | A | T | C |
| 6 | A | G | T | C | G | T | A | T | C |
| 7 | A | A | C | T | G | C | G | T | C |
| 8 | A | G | T | C | G | C | G | T | C |
| 9 | A | A | C | T | G | T | A | C | C |
| 10 | 5 or more haplotypes which are estimated to occur at a frequency of less than 3% | | | | | | | | |

TABLE 2

| Gene name: GIRK3 Haplotype No. | Gene polymorphism name | | | | | | | | | |
|---|---|---|---|---|---|---|---|---|---|---|
| | A-1329C | C-979G | C-968G | A-447G | C1211T | C1339T | C1781T | C1817T | G2069A | C2429T |
| 1 | A | C | G | G | C | C | C | C | G | C |
| 2 | A | C | G | G | C | C | T | T | G | C |
| 3 | A | C | C | A | C | T | T | C | A | T |
| 4 | A | C | C | A | C | C | C | C | G | C |
| 5 | A | C | G | G | C | T | T | C | A | T |
| 6 | A | C | G | G | C | T | T | T | G | C |
| 7 | A | G | C | A | C | T | T | C | A | T |
| 8 | C | C | C | A | C | T | T | C | A | T |
| 9 | A | C | G | G | T | T | T | C | A | T |

<9> A method of determining at least one of type, amount and administration number of drugs to be administered to an individual by using as an index, a result evaluated by the method as described in any of <1> to <8> above.

<10> A method of predicting a side effect of drugs to be administered to an individual by using as an index, a result evaluated by the method as described in any of <1> to <9> above.

<11> The method as described in any of <1>, <2>, <5>, <9> and <10> above,
wherein the drug is at least one of GIRK channel function modulators and mu-opioid receptor function modulators.

<12> The method as described in <11> above,
wherein the GIRK channel function modulator is at least one member selected from the group consisting of morphine, DAMGO, codeine, methadone, carfentanil, fentanyl, heroin, naloxone, naltrexone, nalorphine, levallorphan, pentazocine, pethidine, buprenorphine, oxycodone, hydrocodone, levorphanol, etorphine, dihydroetorphine, hydromorphone, oxymorphone, tramadol, diclofenac, indomethacin, flurbiprofen axetil, marcain, ethanol, methanol, propanol, butanol, flupirtine, laughing gas, F3 (1-chloro-1,2,2-trifluorocyclobutane), halothane, estradiol, dithiothreitol, thioridazine, pimozide, fluoxetine, paroxetine, desipramine, imipramine, clomipramine, tetramide, isoflurane, ginsenoside, ifenprodil, bupivacaine, tertiapine, clozapine, haloperidol, SCH23390 and cocaine, and the mu-opioid receptor function modulator is at least one member selected from the group consisting of methamphetamine, methylenedioxymethamphetamine, amphetamine, dextroamphetamine, dopamine, morphine, DAMGO, codeine, methadone, carfentanil, fentanyl, heroin, cocaine, naloxone, naltrexone, nalorphine, levallorphan, pentazocine, buprenorphine, oxycodone, hydrocodone, levorphanol, etorphine, dihydroetorphine, hydromorphone, oxymorphone, ethanol, methanol, diethyl ether and tramadol.

<13> The method as described in any of <1> to <12> above,
wherein an oligonucleotide which comprises a nucleotide sequence of at least 10 nucleotides containing the 51st nucleotide in a nucleotide sequence represented by any one of SEQ ID NOS: 1 to 19 or a sequence complementary to the nucleotide sequence and is capable of being specifically hybridized to a DNA fragment containing a gene polymorphism in a GIRK channel gene is used.

<14> The method as described in <13> above,
wherein the oligonucleotide has a length of 10 to 150 nucleotides.

<15> The method as described in <13> or <14> above,
wherein the oligonucleotide is an oligonucleotide selected from the group consisting of the nucleotide sequences represented by any of SEQ ID NOS: 1 to 19 and nucleotide sequences complementary to the nucleotide sequences.

<16> An oligonucleotide, which comprises a nucleotide sequence of at least 10 nucleotides containing the 51st nucleotide in a nucleotide sequence represented by any one of SEQ ID NOS: 1, 9, 10, 11 and 14 or a sequence complementary to the nucleotide sequence and is capable of being specifically hybridized to a DNA fragment containing a gene polymorphism in a GIRK channel gene.

<17> The oligonucleotide as described in <16> above, which has a length of 10 to 150 nucleotides.

<18> An oligonucleotide, which is selected from the group consisting of nucleotide sequences represented by any of SEQ ID NOS: 1, 9, 10, 11 and 14 and nucleotide sequences complementary to the nucleotide sequences.

<19> A microarray, in which the oligonucleotide as described in any of <16> to <18> above has been immobilized on a support.

<20> A primer, which comprises a nucleotide sequence represented by any one of SEQ ID NOS: 20 to 25, which is used in detection of a gene polymorphism in the GIRK channel genes in the method as described in any of <1> to <15> above.

<21> A kit for evaluating drug sensitivity, which comprises at least one of: the oligonucleotide as described in any of <16> to <18> above; the microarray as described in <19> above; and the primer as described in <20> above.

<22> A kit for evaluating disease vulnerability, which comprises at least one of: the oligonucleotide as described in any of <16> to <18> above; the microarray as described in <19> above; and the primer as described in <20> above.

DETAILED DESCRIPTION OF THE INVENTION

Hereinafter, the present invention will be described in detail. However, the scope of the invention is not limited to the description, and changes and modifications can be made therein without departing from the spirit of the invention other than the following examples.

1. Outline of the Present Invention (1) GIRK Channel

Narcotic analgesics typified by morphine act on a protein called an opioid receptor thereby to cause analgesia. There are three types of opioid receptors: mu, delta and kappa ($\mu$, $\delta$, $\kappa$), and all receptors are involved in an analgesic action. These receptors are Gi/o protein-coupled receptors, therefore, they not only inhibit adenylate cyclase and calcium channels via a Gi/o protein, but also activate GIRK channels.

In the case where opioid receptors and GIRK channels are artificially expressed in a cell, potassium ions flow out of the cell due to an analgesic such as morphine, which leads to hyperpolarization of the cell membrane. As a result, the activity of the cell is suppressed, and an analgesic effect is exhibited. However, in a weaver mutant mouse having an abnormal GIRK channel which is not controlled by G-protein, an analgesic effect of morphine or the like is decreased. From these findings, in order for an analgesic such as morphine to exhibit a sufficient analgesic effect, opening of GIRK channel is considered to be an extremely important step.

Here, a GIRK channel will be described. The GIRK channel is an ion channel having an important function in regulating excitability of neurons and heart rate and is present in large quantities in the brain and heart. The GIRK channel penetrates the cell membrane twice at M1 and M2 regions and has a structure in which H5 region located between the M1 and M2 regions projects into the cell membrane. The H5 region forms a central portion through which ions pass.

The GIRK channel functions as a tetramer composed of four subunits. There are four types of subunits: GIRK1, GIRK2, GIRK3 and GIRK4. In the brain, GIRK1, GIRK2 and GIRK3 subunits are strongly expressed, and a GIRK1/2 channel by the combination of GIRK1 and GIRK2 subunits mainly functions therein. Incidentally, in the heart, GIRK1 and GIRK4 subunits are strongly expressed, and a GIRK1/4 channel mainly functions therein.

(2) Gene Polymorphism

Figure 1:
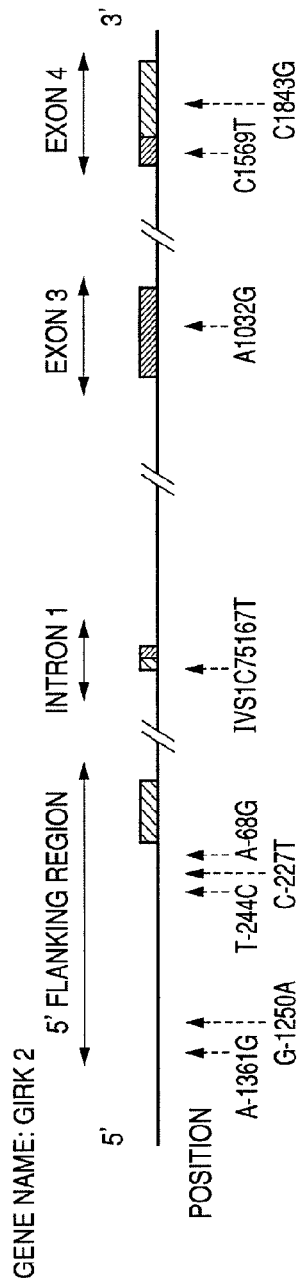
FIG. 1 is a schematic view showing a range of screening GIRK2 subunit gene polymorphisms and identified gene polymorphisms. In the drawing, the shaded portions indicate noncoding regions of the gene, and the solid black portions indicate coding regions of the gene. The upper arrows indicate ranges of screening gene polymorphisms using samples of healthy subjects. The lower arrows indicate names and relative positions of the respective identified gene polymorphisms.
Figure 2:
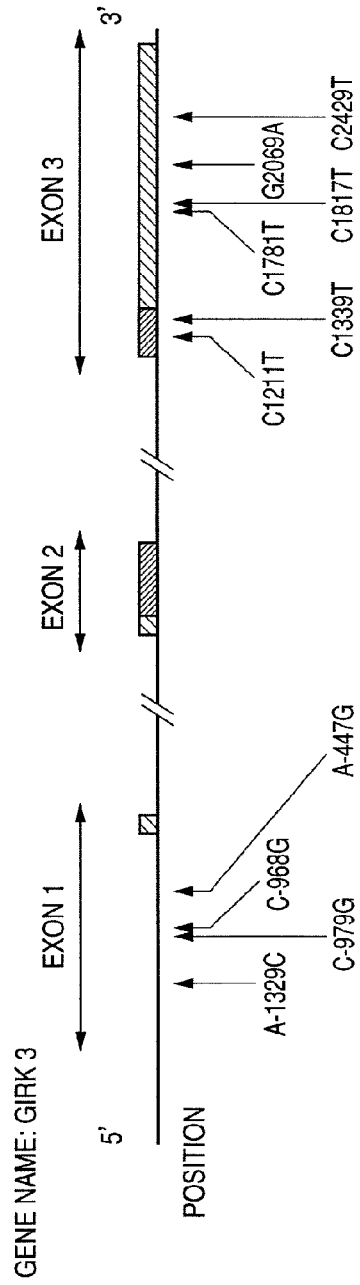
FIG. 2 is a schematic view showing a range of screening GIRK3 subunit gene polymorphisms and identified gene polymorphisms. In the drawing, the shaded portions indicate noncoding regions of the gene, and the solid black portions indicate coding regions of the gene. The lower arrows indicate names and relative positions of the respective identified gene polymorphisms.

The present inventors identified gene polymorphisms (such as SNP) of GIRK2 and GIRK3 subunits, which are expressed strongly in the brain among the four subunits capable of constituting GIRK channels in healthy subjects (FIGS. 1 and 2). Further, a linkage disequilibrium analysis was carried out as needed, and a block exhibiting a strong linkage disequilibrium (a haplotype block) was identified.

Here, the linkage equilibrium means to a case where the relationship between two gene polymorphisms on the chromosome is independent, and the linkage disequilibrium means a case where a gene polymorphism is linked to the other gene polymorphism thereby deviating from the equilibrium situation according to Mendel's law of independence. Further, the haplotype means a genetic structure of such as genes or gene polymorphisms located in the vicinity of each other in one allele of a set of alleles (a gene derived from one of the parents).

Gene polymorphisms or the like located in the vicinity on a genome are inherited in a haplotype block. In other words, a haplotype also refers to a combination of the arrangement of the same gene in this haplotype block.

In the case where several gene polymorphisms appear in association with a certain phenotype in the GIRK channel genes, even if not all the respective gene polymorphisms are typed, by analyzing several gene polymorphisms constituting a haplotype, a relationship between the genotype and the phenotype of a patient can be elucidated.

The present inventors analyzed the GIRK2 subunit gene, and as a result, they found five gene polymorphisms (A-1361G, G1250A, T-244C, C-227T and A-68G) in the 5' flanking region, one gene polymorphism (IVS1C75167T) in a portion of intron, and one gene polymorphism each (three gene polymorphisms in total: A1032G, C1569T and C1843G) in the coding region of exon 3, the coding region of exon 4 and the 3' noncoding region (see FIG. 1). Among these gene polymorphisms, a gene polymorphism with a high minor allele frequency in the exons was A1032G.

Further, with regard to the GIRK3 subunit gene, they found four gene polymorphisms (A-1329C, C979G, C-968G and A-447G) in the 5' flanking region, two gene polymorphisms (C1211T and C1339T) in the coding region of exon 3, and four gene polymorphisms (C1781T, C1817T, G2069A and C2429T) in the 3' noncoding region (see FIG. 2). Among these gene polymorphisms, gene polymorphisms with a particularly high minor allele frequency in the exons were C1339T, C1781T and the like, and further, a gene polymorphism with an amino acid substitution was only C1339T.

In particular, two gene polymorphisms: A-1361G and C1843G in the GIRK2 subunit gene, and three gene polymorphisms: A-1329C, C-979G and C1211T in the GIRK3 subunit gene were new gene polymorphisms which were not registered in the GenBank database.

By analyzing gene polymorphisms or haplotypes in GIRK channel genes, an individual difference in drug sensitivity or disease vulnerability such as the required number of administration of analgesics, total amount of analgesics, vulnerability to drug dependence or prolongation of stimulant-induced psychosis can be easily evaluated. The results of evaluating drug sensitivity or disease vulnerability can be important information for determining the administration number, amount, type or the like of drugs to be administered to an individual, and predicting side effects.

In particular, because morphine, a stimulant or the like may cause a big social problem depending on the usage, it is important to know in advance an appropriate amount of drugs to be administered to an individual before administering the drugs. Therefore, the present invention is extremely useful for personalized pain therapy or drug dependence therapy.

2. GIRK Channel Gene Polymorphism

The human GIRK channel gene polymorphisms of the present invention include mainly single nucleotide polymorphisms (hereinafter also referred to as SNP), however it is not limited to this, and insertion polymorphisms, deletion polymorphisms, and nucleotide repeat polymorphisms can also be included.

The single nucleotide polymorphism (SNP (SNPs)) means a gene polymorphism caused by substitution of a specific one nucleotide of a gene with another nucleotide. The insertion/deletion polymorphism means a gene polymorphism caused by deletion/insertion of one or more nucleotides.

Further, the nucleotide repeat polymorphism means a gene polymorphism caused by a difference in the number of repeats of nucleotide sequence. The nucleotide repeat polymorphism is divided into a microsatellite polymorphism (the number of nucleotides: about 2 to 4 nucleotides) and a VNTR (variable number of tandem repeat) polymorphism (repeated nucleotides: several to several tens of nucleotides) according to the difference in the number of repeated nucleotides, and the number of repeats varies depending on individuals.

The information of human GIRK channel gene polymorphisms (SNPs in GIRK2 and GIRK3 observed on the genome of Japanese healthy subjects) elucidated by the present invention is shown in Table 3. The gene polymorphisms shown in Table 3 are included in the GIRK channel gene polymorphisms of the present invention.

TABLE 3

| Gene name | Position | Gene polymorphism name | Major allele | Minor allele |
|---|---|---|---|---|
| GIRK2 | 5' flanking region | A-1361G | A | G |
| | | G-1250A | A | G |
| | | T-244C | C | T |
| | | C-227T | T | C |
| | | A-68G | G | A |
| | Intron 1 | IVS1C75167T | T | C |
| | Exon 3 | A1032G | G | A |
| | Exon 4 | C1569T | T | C |
| | | C1843G | C | G |

TABLE 3-continued

| Gene name | Position | Gene polymorphism name | Major allele | Minor allele |
|---|---|---|---|---|
| GIRK3 | 5' flanking region | A-1329C | A | C |
| | | C-979G | C | G |
| | | C-968G | G | C |
| | | A-447G | G | A |
| | Exon 3 | C1211T | C | T |
| | | C1339T | C | T |
| | | C1781T | C | T |
| | | C1817T | C | T |
| | | G2069A | G | A |
| | | C2429T | C | T |

In Table 3, "Gene name" means the name of a gene encoding a subunit capable of constituting a human GIRK channel, and for example "GIRK2" (italic form) indicates the GIRK2 subunit gene. Incidentally, the GIRK2 gene is also referred to as Kir3.2 gene and sometimes represented by "KCNJ6" (italic form), and the GIRK3 gene is also referred to as Kir3.3 gene and sometimes represented by "KCNJ9" (italic form).

"Position" means a position on the genome of a GIRK channel gene, and indicates a 5' flanking region, as well as each exon and intron.

"Gene polymorphism name" is the name of SNP at a position on the genome and given by the present inventors. Basically, an alphabet of A, G, C or T is given before and after two- to five-digit number and symbol, respectively, thus which nucleotide is involved in SNP can be identified. For example, "A-1361G" indicates a gene polymorphism in which the nucleotide located 1361 bp upstream (5' side) of the transcription start site is changed between A and G. "C1339T" indicates a gene polymorphism in which the nucleotide located 1339 bp downstream (3' side) of the transcription start site is changed between C and T.

Here, with regard to how to count the number of nucleotides from the transcription start site, when the nucleotide at the transcription start site is determined to be 1, the nucleotide located one nucleotide upstream of the transcription start site is determined to be −1 and the nucleotide located one nucleotide downstream of the transcription start site is determined to be 2. In the same manner, the nucleotides are counted sequentially.

Further, "IVS1C75167T" in the column of "Intron 1" indicates a gene polymorphism in intron 1, in which the nucleotide at the start site in intron 1 is determined to be 1, and the nucleotide located 75167 bp downstream thereof is changed between C and T.

"Major allele" indicates an allele occurring in the majority of the genomes of Japanese healthy subjects, and "minor allele" indicates an allele occurring in the minority of the genomes of Japanese healthy subjects.

In the present invention, a method of obtaining gene polymorphism information is as follows, for example.

(1) Genomic DNA is purified from a blood specimen collected from a human using the phenol method and the like. At this time, a commercially available genomic DNA extraction kit such as GFX Genomic Blood DNA Purification Kit (manufactured by GE Healthcare Bio-Sciences KK) or a device may be used.

(2) Then, a part of the genomic DNA is amplified by the PCR method using the genomic DNA as a template, thereby to prepare a template DNA for sequencing. The present invention is directed to a gene polymorphism, therefore, it is preferred that an enzyme with a fidelity of as high as possible is used in the PCR method.

(3) With regard to the 5' noncoding region (5' UTR) and 5' flanking region of the GIRK channel gene, the full length of a region located up to about 1.8 kbp, preferably about 2 kbp upstream of the transcription start site or fragments obtained by dividing the region into 2 to 4 regions is/are amplified by PCR. With regard to the respective exons and intron, the full region is amplified for each region by the PCR method.

(4) In the case when the final exon (an exon which is the closest to the 3' end) is amplified, a region containing the coding region up to the stop codon and 3' noncoding region (3' UTR) is divided into 2 to 5 regions, and amplification is carried out by PCR.

(5) The nucleotide sequences of the full regions of these PCR fragments are analyzed such that a segment of about 500 to 700 bp was decoded by the sequencing method at a time using primers designed based on the sequence information published in GenBank, whereby gene polymorphism information of interest can be obtained.

The present invention provides an oligonucleotide which contains any one of GIRK2 subunit gene polymorphisms (A-1361G, G-1250A, T-244C, C-227T, A-68G, IVS1C75167T, A1032G, C1569T and C1843G) and GIRK3 subunit gene polymorphisms (A-1329C, C-979G, C-968G, A-447G, C1211T, C1339T, C1781T, C1817T, G2069A and C2429T), and is capable of being specifically hybridized to a DNA fragment containing a gene polymorphism in the GIRK channel genes. The gene polymorphic site is the 51st nucleotide in the nucleotide sequence represented by any one of SEQ ID NOS: 1 to 19.

It is preferred that the oligonucleotide of the present invention has at least 10 nucleotides, preferably 10 to 150 nucleotides, more preferably 10 to 45 nucleotides, further more preferably 14 to 25 nucleotides.

Examples of the oligonucleotide of the present invention include oligonucleotides having a nucleotide sequence represented by any one of SEQ ID NOS: 1 to 19 containing the above-mentioned gene polymorphism or a nucleotide sequence complementary to the nucleotide sequence (Table 4).

The oligonucleotides of the present invention can be used as a probe or a primer specific to a GIRK channel gene in the detection of GIRK channel gene polymorphism described in the below-mentioned 5.

TABLE 4

| Gene name | Position | Gene polymorphism name | Sequence | | SEQ ID NO |
|---|---|---|---|---|---|
| GIRK2 | 5' flanking region | A-1361G | TATGACTCAGAAGTAATAGCAAGTCAGATTACAACCTCTTAGGGAAAATC ACAGCAAATACAAGCTCACAGGCCGTGTGTACGGTTGACTTTTACATGAC | A/G | 1 |
| | | G-1250A | AATTGACACAAACACCTCTCCATATTACAGTCATTTTTAGAGGGCAGACA CATTCTTGAGGGGACCTGAATTGCTAGGTAATTAAAATGTATGTATGTAG | G/A | 2 |
| | | T-244C | AGATTCCCCCAGCATGGAGCACCCACGTTTCCAGTGGCGGGGATGCACG TGGTTTGTGCCCAGCCCGCCCCCACCAAGCCCGGTCCTCGACGCGCTGAC | T/C | 3 |
| | | C-227T | AGCACCCACGTTTCCAGTGGCGGGGATGCACGTTGGTTTGTGCCCAGCC GCCCCCACCAAGCCCGGTCCTCGACGCGCTGACACGCTAGCTGGCATGGG | C/T | 4 |
| | | A-68G | CCCGGACCGCGCCGGCGCTGTGCGGCTTTTTCCCCAGCACGCGGCGCTGC CTCGCTTTTATCTCGGAGCCGCGTCGCTTCGTGCGCTGCCAGCGGGGCTC | A/G | 5 |
| | Intron 1 | IVS1C75167T | AGATCAATTCATATCTAAGACATGTTTTACAGATAATTGTCTTTTCTTCT ACCTCCAGGAAAAGCACAAAGAAGAAACTGCAACAATGGCCAAGCTGACA | C/T | 6 |
| | Exon 3 | A1032G | ACAGAAACCACCATTGGTTATGGCTACCGGGTCATCACAGATAAATGCCC GAGGGAATTATTCTTCTCTTAATCCAATCTGTGTTGGGGTCCATTGTCAA | A/G | 7 |
| | Exon 4 | C1569T | AGTGAGATCCTGTGGGGTTACCGGTTCACACCTGTCCTGACCCTGGAGGA GGGTTCTACGAAGTTGACTACAACAGCTTCCATGAGACCTATGAGACCAG | C/T | 8 |
| | | C1843G | ATGAATCCAAAGTTTAGTGCCCTAGCTGGGCAAACCCTTCTCTTCTCCCC CAACACAATCTTTCCTTGTCTCTCATTCTCTTTCTTTTTCTGTCTCTCTT | C/G | 9 |
| GIRK3 | 5' flanking region | A-1329C | TTATATATTTGTCCAAACCCACAGAGTGTACAACACCAAAAGTGAACCCT ATGTCAGCTATGGACTTTGGGCGATTATGATGTCAATGTAGCTTCATCAC | A/C | 10 |
| | | C-979G | TAACACCTGTCTTATAGAGTTGCCATGGGGATGACATGAGGCATGTGTCT GTTCATATCCCATGCTCAGTGAATTAGTAGCAGCAGCCACTGTGTGTTTG | C/G | 11 |
| | | C-968G | TTATAGAGTTGCCATGGGGATGACATGAGGCATGTGTCTCGTTCATATCC ATGCTCAGTGAATTAGTAGCAGCAGCCACTGTGTGTTTGTGTGTCTTTAT | C/G | 12 |
| | | A-447G | TTCCTTCTAGCTACCGCCTTCTGGATCCATGGCCTCTCCAAAACTAGACC TGATGGTCAGCCTGACCTGAGAGCAGCACCTGCACGCAGAGACCCATGTT | A/G | 13 |
| | Exon 3 | C1211T | GTGCTGACTCTGGAGGACGGCTTCTACGAAGTGGACTATGCCAGCTTTCA GAGACTTTTGAGGTGCCCACACCTTCGTGCAGTGCTCGAGAGCTGGCAGA | C/T | 14 |
| | | C1339T | CTACTGGTCCATCCCCAGCCGGCTGGATGAGAAGGTGGAGGAGGAGGGGG GGGGGAGGGGCGGGTGGGGAAGCTGGGGCTGACAAGGAGCAGAATGGCT | C/T | 15 |

TABLE 4-continued

| Gene name | Position | Gene polymorphism name | Sequence | SEQ ID NO |
|---|---|---|---|---|
| | | C1781T | TGGTAGCAGATAAAGACAGCTGACAGATACATAGATGGACCAGTAGACAA C/T TGGTCCACTCAGGGCTGCCACTAACCTGTAGAACACCCCTGTGCAAATTT | 16 |
| | | C1817T | GGACCAGTAGACAACTGGTCCACTCAGGGCTGCCACTAACCTGTAGAACA C/T CCCTGTGCAAATTTTAAAAAGGAACCCTTTTCCTCCAGACAGATACAGCC | 17 |
| | | G2069A | GGCACATGAGGAGGGTGCCCTCCTAGCTCCACCCTCACCAGGATGAAGGC G/A TGCAAGGGGCTCAGCAAGGTGTGAATGACCTTAGTCCGCAAGTTCAGGGA | 18 |
| | | C2429T | CATGTGGAGTGGACATTCAAAAACCTGGTTCCTGTCCTCAAAATAAGGGG C/T ACCTGGGAAAACAGAGGAATCTACCTGTGGTGACTGAACGAGGGATAATT | 19 |

In Table 4 (SEQ ID NOS: 1 to 19), 101 nucleotides are shown, and a gene polymorphic site is shown at the 51st nucleotide. For example, one represented by "A/G" means a gene polymorphism associated with transitions between "A" and "G", and "C/T" means a gene polymorphism associated with transitions between "C" and "T".

3. Haplotype Analysis

In the present invention, by using SNP among the above-mentioned gene polymorphisms, a haplotype can be constructed. The SNP to become a target of a haplotype analysis may be any as long as its gene polymorphism frequency is 0.5% or higher, preferably, those with a gene polymorphism frequency of 1%, more preferably those with a gene polymorphism frequency of 5% or higher can be selected. Further, SNP to become a target of a haplotype analysis may be a full or partial sequence thereof.

The haplotype analysis can be carried out using various computer programs, and for example, Haplotype Estimation (available from the website: www.bioinf.mdc-berlin.de/projects/hap/: www.bioinf.mdc-berlin.de/projects/hap/ Rohde K, Fuerst R: Haplotyping and estimation of haplotype frequencies for closely linked biallelic multilocus genetic phenotypes including nuclear family information. Max-Delbrueck-Centrum for Molecular Medicine, Berlin, Germany) can be used.

As an example of the haplotype analysis, with regard to the 9 sites of SNPs which are GIRK2 subunit gene polymorphisms and the 10 sites of SNPs which are GIRK3 subunit gene polymorphisms among the GIRK channel gene polymorphisms in Japanese healthy subjects found as in the above-mentioned 2, a haplotype was estimated using Haplotype Estimation. The estimated haplotypes are shown in Tables 5 and 6.

TABLE 5

| Gene name: GIRK2 Haplotype No. | Gene polymorphism name | | | | | | | | |
|---|---|---|---|---|---|---|---|---|---|
| | A-1361G | G-1250A | T-244C | C-227T | A-68G | IVS1 C75167T | A1032G | C1569T | C1843G |
| 1 | A | A | C | T | G | T | G | T | C |
| 2 | A | G | T | C | G | T | G | T | C |
| 3 | A | A | C | T | G | T | A | T | C |
| 4 | A | G | T | C | A | T | G | T | C |
| 5 | A | A | C | T | G | C | A | T | C |
| 6 | A | G | T | C | G | T | A | T | C |
| 7 | A | A | C | T | G | C | G | T | C |
| 8 | A | G | T | C | G | C | G | T | C |
| 9 | A | A | C | T | G | T | A | C | C |
| 10 | 5 or more haplotypes which are estimated to occur at a frequency of less than 3% | | | | | | | | |

TABLE 6

| Gene name: GIRK3 Haplotype No. | Gene polymorphism name | | | | | | | | |
|---|---|---|---|---|---|---|---|---|---|
| | A-1329C | C-979G | C-968G | A-447G | C1211T | C1339T | C1781T | C1817T | G2069A | C2429T |
| 1 | A | C | G | G | C | C | C | C | G | C |
| 2 | A | C | G | G | C | C | T | T | G | C |
| 3 | A | C | C | A | C | T | T | C | A | T |
| 4 | A | C | C | A | C | C | C | C | G | C |
| 5 | A | C | G | G | C | T | T | C | A | T |
| 6 | A | C | G | G | C | T | T | T | G | C |
| 7 | A | G | C | A | C | T | T | C | A | T |
| 8 | C | C | C | A | C | T | T | C | A | T |
| 9 | A | C | G | G | T | T | T | C | A | T |

Further, from the genotype information of GIRK genes of the respective individuals in a population, a haplotype frequency in the population is calculated, and a linkage disequilibrium analysis can be carried out based on the thus obtained haplotype frequency. The D' value and $r^2$ value, which indicate measures of linkage disequilibrium, can be calculated based on the following definition.

Definition

It is assumed that there are SNP A and SNP B, and the respective alleles are represented by A and a, and B and b. The four haplotypes formed by SNP A and SNP B are represented by AB, Ab, aB and ab, and the respective haplotype frequencies are represented by $P_{AB}$, $P_{Ab}$, $P_{aB}$ and $P_{ab}$.

$$D = P_{AB} \times P_{ab} - P_{Ab} \times P_{aB} \text{ (In the case of D>0)}$$

$$D' = (P_{AB} \times P_{ab} - P_{Ab} \times P_{aB})/\text{Minimum}(((P_{AB}+P_{aB}) \times (P_{aB}+P_{ab})), ((P_{AB}+P_{Ab}) \times (P_{Ab}+P_{ab}))) \text{ (In the case of D<0)}$$

$$D' = (P_{AB} \times P_{ab} - P_{Ab} \times P_{aB})/\text{Minimum}(((P_{AB}+P_{aB}) \times (P_{AB}+P_{Ab})), ((P_{aB}+P_{ab}) \times (P_{Ab}+P_{ab})))$$

$$r^2 = (P_{AB} \times P_{ab} - P_{Ab} \times P_{aB})^2 / \{(P_{AB}+P_{Ab})(P_{AB}+P_{aB})(P_{aB}+P_{ab})(P_{Ab}+P_{ab})\} \text{ [However, Minimum}(((P_{AB}+P_{aB}) \times (P_{aB}+P_{ab})), ((P_{AB}+P_{Ab}) \times (P_{Ab}+P_{ab}))) \text{ means that a smaller value among } (P_{AB}+P_{aB}) \times (P_{aB}+P_{ab}) \text{ and } (P_{AB}+P_{Ab}) \times (P_{Ab}+P_{ab}) \text{ is adopted.]}$$

Further, a haplotype block can be estimated from the results of the linkage disequilibrium analysis. As for the haplotype block, a linkage block can be estimated from the results of the haplotype analysis by using, for example, Haploview (which is accessible from www.broad.mit.edu/mpg/haploview/index.php).

When a specific SNP in the estimated haplotype blocks is examined, the information of SNPs indirectly linked to each other in the same block can be obtained. That is, when a gene polymorphism of the GIRK channel (specifically, GIRK2 or GIRK3 subunit) gene is examined, it is not necessary to analyze all the SNPs, and it is only necessary to perform typing for several specific SNPs.

4. Correlation Between GIRK Channel Gene Polymorphism and Drug Sensitivity or Disease Vulnerability It is considered that when a gene polymorphism occurs in the GIRK channel gene, the function or expression level of GIRK channel might change. Therefore, there is a correlation between a GIRK channel gene polymorphism and various phenotypes associated with the GIRK channel in some cases.

Here, as the phenotype, a phenotype associated with sensitivity to drugs (drug sensitivity) and a phenotype associated with occurrence of a disease (disease vulnerability) can be exemplified. As the drug sensitivity, an efficacy of drugs, a side effect of drugs, duration of efficacy of drugs and the like can be exemplified. As the disease vulnerability, pain sensitivity, vulnerability to drug dependence and the like can be exemplified.

The drugs is preferably drugs associated with GIRK, and examples thereof include various drugs acting directly or indirectly on the GIRK channel. Examples of the various drugs acting directly or indirectly on the GIRK channel include a GIRK channel function modulator, an opioid receptor function modulator and the like, and preferred is a GIRK channel function modulator. Specific examples thereof include a stimulant such as methamphetamine, a dopamine receptor agonist, a dopamine receptor antagonist, a μ-, κ-, or δ-opioid receptor agonist, a μ-, κ-, or δ-opioid receptor antagonist and the like.

Examples of the GIRK channel function modulator include morphine, DAMGO, codeine, methadone, carfentanil, fentanyl, heroin, naloxone, naltrexone, nalorphine, levallorphan, pentazocine, pethidine, buprenorphine, oxycodone, hydrocodone, levorphanol, etorphine, dihydroetorphine, hydromorphone, oxymorphone, tramadol, diclofenac, indomethacin, flurbiprofen axetil, marcain, ethanol, methanol, propanol, butanol, flupirtine, laughing gas, F3 (1-chloro-1,2,2-trifluorocyclobutane), halothane, estradiol, dithiothreitol, thioridazine, pimozide, fluoxetine, paroxetine, desipramine, imipramine, clomipramine, tetramide, isoflurane, ginsenoside, ifenprodil, bupivacaine, tertiapine, clozapine, haloperidol, SCH23390, cocaine and the like. In particular, morphine, pentazocine, pethidine, buprenorphine, diclofenac, indomethacin, flurbiprofen axetil and marcain are preferred, and morphine, fentanyl and pentazocine are more preferred.

Examples of the mu-opioid receptor function modulator include methamphetamine, methylenedioxymethamphetamine, amphetamine, dextroamphetamine, dopamine, morphine, DAMGO, codeine, methadone, carfentanil, fentanyl, heroin, cocaine, naloxone, naltrexone, nalorphine, levallorphan, pentazocine, buprenorphine, oxycodone, hydrocodone, levorphanol, etorphine, dihydroetorphine, hydromorphone, oxymorphone, ethanol, methanol, diethyl ether, tramadol and the like. In particular, methamphetamine, morphine, pentazocine and buprenorphine are preferred, and morphine, fentanyl and pentazocine are more preferred.

The correlation between a GIRK channel gene polymorphism and a phenotype can be examined as described in the following (1) to (4), for example.

(1) A gene polymorphism in a linkage disequilibrium block estimated as a result of a linkage disequilibrium analysis and a haplotype analysis in healthy subjects is selected. For example, a Tag SNP which is a typical gene polymorphism is selected as a GIRK channel gene polymorphism for analyzing a correlation with a phenotype.

(2) Then, a gene polymorphism frequency of the gene polymorphism in test subjects (patients) is analyzed. In the case where a correlation between a gene polymorphism and disease vulnerability is examined, comparison of gene polymorphisms between the test subjects and the healthy subjects is carried out. It is effective to use a statistical technique such as a chi-square test in the comparison.

Here, the test subjects are classified into groups depending on the difference in phenotypes, and comparison of gene polymorphism frequencies or genotypes between healthy subjects and test subjects can be carried out for each group. In the case where the phenotype associated with the occurrence of a disease is a stimulant-induced psychotic-like symptom, it can be classified, for example, according to a period of time from the start of the use of a stimulant to the occurrence of delusion or hallucination, a period of duration of delusion or hallucination after termination of the use thereof, the presence or absence of the relapse, and the presence or absence of multiple drug abuse.

(3) If there is a gene polymorphism significantly linked to drug sensitivity in the test subjects, the gene polymorphism can be used for evaluating the genetic predisposition to drug sensitivity. Further, if there is a gene polymorphism with a significant difference in the gene polymorphism frequency between the healthy subjects and the test subjects, the gene polymorphism can be used for evaluating the genetic predisposition to disease vulnerability.

However, it is suggested that the tendency of gene polymorphism is affected by the race, birthplace or the like, therefore, it is preferred that in a group showing a similar gene polymorphism to that of a population used for finding an associated gene polymorphism (such as SNP), the above-mentioned evaluation using the gene polymorphism is carried out.

Specific examples of the correlation between a GIRK channel gene polymorphism and a phenotype will be shown in the following (1) to (4).

(1) In a group of patients who did not have a major allele (G) of the GIRK2 subunit gene polymorphism (A1032G) and underwent surgery, the required number of administration of analgesics was statistically significantly higher compared with a group of patients who had the allele (G). In addition, there was a tendency that the total amount of analgesics was statistically large in the group of patients who did not have the major allele (G) of the gene polymorphism, and in particular, in female patients, the total amount of analgesics was statistically significantly large. Thus, by analyzing the GIRK2 subunit gene polymorphism (A1032G), the sensitivity to analgesics can be predicted.

(2) In the correlation with the required number of administration of analgesics and the total amount of analgesics after surgery, the presence or absence of a major allele (G) of the GIRK2 subunit gene polymorphism (A1032G) and the presence or absence of a major allele (A) of G-1250A showed a significant interaction. Thus, by analyzing the GIRK2 subunit gene polymorphism (A1032G) and the GIRK2 subunit gene polymorphism (G-1250A), the sensitivity to analgesics can be predicted more precisely.

(3) In a group of methamphetamine-dependent patients, the frequency of a minor allele (T) of the GIRK3 subunit gene polymorphism (C1339T) which is a nonsynonymous substitution was significantly higher compared with a group of healthy subjects. Thus, by analyzing the GIRK3 subunit gene polymorphism (C1339T), the dependence on methamphetamine can be predicted.

(4) Between a group of patients with prolonged stimulant-induced psychosis (for one month or more) and a group of healthy subjects, a significant difference was observed in both gene polymorphism frequency and allele frequency in terms of the gene polymorphism (C1339T) in the GIRK3 subunit gene. Thus, by analyzing the gene polymorphism (C1339T) in the GIRK3 subunit gene, disease vulnerability to stimulant-induced psychosis can be predicted.

5. Use of Analysis Results

As in the above-mentioned 4, the correlation between a GIRK channel gene polymorphism and a phenotype analyzed can be used as an index in a method of predicting sensitivity to various drugs associated with the GIRK channel, a method of selecting a method of treating or preventing a disease associated with the GIRK channel, a method of determining an appropriate administration amount of therapeutic drugs, a method of predicting side effects or the like.

Further, by using the gene polymorphism or the method of the present invention, it is possible to evaluate drug sensitivity or disease vulnerability in different races. The subjects are not particularly limited and examples thereof include Japanese, Europeans, Americans and the like, however, in the present invention, they are preferably Japanese or those having a similar gene polymorphism tendency to that of Japanese.

6. Detection of Gene Polymorphism

A genome sample of a test subject can be extracted from the blood, saliva, skin or the like, however, the origin is not limited to these as long as a genome sample can be collected therefrom. The extraction and purification methods of genomic DNA are publicly well known. For example, genomic DNA is purified from a specimen such as the blood, saliva, skin or the like collected from a human using the phenol method or the like. At this time, a commercially available genomic DNA extraction kit such as GFX Genomic Blood DNA Purification Kit (manufactured by GE Healthcare Bio-Sciences KK) or a device may be used. In the case where SNP to be detected is present in an exon, mRNA or total RNA may be extracted instead of genomic DNA.

In the detection of GIRK channel gene polymorphism in a genome sample, the above-mentioned oligonucleotide of the present invention can be used as a probe or a primer. Hereinafter, an example of the gene polymorphism detection method will be described.

(1) Detection of Gene Polymorphism Using the PCR Method

In order to amplify a test sample by PCR, it is preferred that a high fidelity DNA polymerase, for example, KOD Dash polymerase (manufactured by TOYOBO) is used. A primer to be used is designed such that a target SNP in the test sample can be amplified and synthesis is carried out. It is preferred that a gene polymorphism or a strand complementary thereto is contained at a given position between the forward and reverse primers. After completion of the amplification reaction, detection of the amplified products is carried out, and the presence or absence of a gene polymorphism is determined.

Preferred examples of the primer which can be used in the method of the present invention include primers shown in the following Table 7.

TABLE 7

| Gene name | Position | Gene polymorphism name | Primer sequence for PCR amplification (5' > 3') | SEQ ID NO |
|---|---|---|---|---|
| GIRK2 | 5' flanking region | G-1250A | CAGGCATTGTGGAGCACGTATTAC | 20 |
|  |  |  | CACCCCTCTTTTTCTTATGGTCA | 21 |
|  | Exon 3 | A1032G | TTCTCAATAGAGACAGAAACCACCATTGGTTAT GGCTACCGGGTCATCACAGATAAATGT | 22 |
|  |  |  | GACACCAGAAACAGACGGTCATC | 23 |
| GIRK3 | Exon 3 | C1339T | TTGGGGCAAATGGAGAAGACACGAG | 24 |
|  |  |  | GGACCCCTCCCTTCCATACTGGTTT | 25 |

(2) Detection of Gene Polymorphism by the Sequencing Method

The gene polymorphism of the present invention can also be detected by a sequencing method based on the dideoxy method. As a sequencer to be used for the sequencing, a commercially available ABI series (Applied Biosystems) can be used.

(3) Detection of Gene Polymorphism by a DNA Microarray

A DNA microarray is a microarray in which oligonucleotide probes have been immobilized on a support, and includes a DNA chip, a Gene chip, a microchip, a bead array and the like. First, a polynucleotide of a test sample is isolated and amplified by PCR, and then labeled with a fluorescent reporter group. Then, a labeled DNA/mRNA, or total RNA is incubated along with an array.

Then, this array is inserted in a scanner, and a hybridization pattern is detected. The data of the hybridization is collected as emitted light from the fluorescent reporter group bound to the probe array (i.e., incorporated in a target sequence). A probe which is completely identical with the target sequence generates a stronger signal than those having a region which is not identical with the target sequence. Because the sequence and the position of each probe on the array are known, the sequence of the target polynucleotide reacted with the probe array can be determined based on the complementarity.

(4) Detection of Gene Polymorphism by the TaqMan PCR Method

The TaqMan PCR method is a method utilizing an allele specific oligonucleotide (also referred to as TaqMan probe) labeled with fluorescence and PCR with Taq DNA polymerase. The allele specific oligonucleotide is an oligonucleotide containing a gene polymorphic site. The allele specific oligonucleotide to be used in the TaqMan PCR method can be designed based on the above-mentioned gene polymorphism information.

(5) Detection of Gene Polymorphism by the Invader Method

The invader method is a method of detecting a gene polymorphism by subjecting an allele specific oligonucleotide and a template to hybridization. A kit for carrying out the invader method is commercially available (for example, Nano Invader® Array (manufactured by BML, Inc.)), and it is possible to easily detect a gene polymorphism by this method.

6. Kit

The present invention provides a kit for evaluating drug sensitivity or disease vulnerability. The kit for detecting a gene polymorphism of the present invention includes one or more components necessary for carrying out the present invention.

For example, the kit of the present invention preferably includes a component for storing or supplying an enzyme and/or a reaction component necessary for detecting a gene polymorphism. Such a component is not limited, however, examples thereof include the oligonucleotide of the present invention, an enzyme buffer solution, dNTP, a reagent for control (such as a tissue sample or a target oligonucleotide for a positive or negative control), a reagent for labeling and/or detection, a solid phase support, a written instruction manual and the like. Further, the kit of the present invention may be a partial kit including only a part of the necessary components. In this case, a user can prepare the other components.

The kit of the present invention can be provided as a microarray in which the above-mentioned oligonucleotide has been immobilized on a support. The microarray is one in which the oligonucleotide of the present invention has been immobilized on a support, and includes a DNA chip, a Gene chip, a microchip, a bead array and the like.

The kit of the present invention preferably includes an oligonucleotide which contains a GIRK channel gene polymorphism found in the present invention and is capable of being specifically hybridized to a DNA fragment containing the gene polymorphism.

In the case where a gene polymorphism is determined using the kit of the present invention, for example, the blood is collected before drugs are applied to patients or the like (for example, before surgery, at the time of occurrence of cancer pain or the like), and DNA containing a GIRK channel gene is isolated. Then, this gene is reacted with an oligonucleotide in the kit, whereby a genotype is determined.

Further, the kit of the present invention may include a primer composed of a nucleotide sequence represented by any one of SEQ ID NOS: 20 to 25 to be used in the detection of a GIRK channel gene polymorphism. The detection of a GIRK channel gene polymorphism using the primer is carried out by, for example, PCR.

From the determined genotype and gene polymorphism, a dosage regimen such as the type or dose of the drugs can be designed. As a result, an effect of the drugs suitable for an individual can be obtained, which is useful in the personalized medicine. For example, in the case of using morphine, it becomes possible to obtain an analgesic effect suitable for an individual, and also to suppress the side effects to the minimum.

Hereinafter, the present invention will be described in more detail with reference to Examples, however, the invention is not limited to these.

Example 1

SNP Analysis and Haplotype Construction (SNP Analysis)

Genomic DNA was extracted from the blood or the oral mucosa of humans (48 Japanese healthy subjects) by a standard method, and gene polymorphisms were identified in two subunits (GIRK2 and GIRK3) which were strongly expressed mainly in the brain among four subunits of human G protein-activated inwardly rectifying potassium channel (GIRK channel).

With regard to the GIRK2 subunit, an entire exon region, a 5' flanking region, and a part of an intron region were analyzed. The GIRK2 subunit gene includes four exons, and three gene polymorphisms in total, i.e., one gene polymorphism in each of a coding region of exon 3, a coding region of exon 4 and a 3' noncoding region of exon 4 were identified in the Japanese samples. Further, five gene polymorphisms were found in the 5' flanking region, and one gene polymorphism was found in the intron (see FIG. 1 and Table 8). As a result of linkage disequilibrium analysis, three gene polymorphisms in the 5' flanking region were found to show a strong linkage disequilibrium. It was found that G-1250A was suitable as a Tag SNP representing this linkage disequilibrium block.

Further, in the same manner as above, with regard to the GIRK3 subunit gene, an entire exon region, the 5' flanking region, and a part of an intron region were analyzed. The GIRK3 subunit gene includes three exons, and two gene polymorphisms in the coding region of exon 3, four gene polymorphisms in the 3' noncoding region of exon 3, and four gene polymorphisms in the 5' flanking region were identified in the Japanese samples (see FIG. 2 and Table 8). Among these gene polymorphisms, gene polymorphisms with a particularly high minor allele frequency in the exons were C1339T, C1781T and the like, and a gene polymorphism with an amino acid substitution was only C1339T.

TABLE 8

| Gene name | Position | Gene polymorphism name | Major allele | Minor allele | Reported allele | Amino acid substitution | Minor allele frequency | Number of test subjects (subjects) |
|---|---|---|---|---|---|---|---|---|
| GIRK2 | 5' flanking region | A-1361G | A | G | A | — | 0.010 | 48 |
| | | G-1250A | A | G | G | — | 0.385 | 48 |
| | | T-244C | C | T | T | — | 0.391 | 46 |
| | | C-227T | T | C | C | — | 0.391 | 46 |
| | | A-68G | G | A | A | — | 0.089 | 45 |
| | Intron 1 | IVS1C75167T | T | C | C | — | 0.188 | 48 |
| | Exon 3 | A1032G | G | A | A | — | 0.344 | 48 |
| | Exon 4 | C1569T | T | C | C | — | 0.062 | 48 |
| | | C1843G | C | G | C | — | 0.052 | 48 |
| GIRK3 | 5' flanking region | A-1329C | A | C | A | — | 0.010 | 48 |
| | | C-979G | C | G | C | — | 0.010 | 48 |
| | | C-968G | G | C | C | — | 0.202 | 47 |
| | | A-447G | G | A | A | — | 0.202 | 47 |
| | Exon 3 | C1211T | C | T | C | — | 0.010 | 48 |
| | | C1339T | C | T | C | Ala366Val | 0.250 | 48 |
| | | C1781T | C | T | C | — | 0.438 | 48 |
| | | C1817T | C | T | C | — | 0.208 | 48 |
| | | G2069A | G | A | G | — | 0.229 | 48 |
| | | C2429T | C | T | C | — | 0.229 | 48 |

In Table 8, "Reported allele" indicates an allele of the sequence registered in GenBank. "Amino acid substitution" means that the type of amino acid after translation is changed depending on the gene polymorphism allele. For example, "Ala366Val" indicates that the amino acid at the position 366 from the N terminus of the peptide chain after translation is substituted with alanine or valine. Incidentally, the symbol "-" means that the type of amino acid is not changed even in any allele.

As shown in Table 8, "minor allele frequency" means the ratio of a minor allele. "Number of test subjects" means the number of healthy subjects to become test subjects.

(Haplotype Construction)

As an example of haplotype analysis, with regard to the 9 sites of SNPs which are GIRK2 subunit gene polymorphisms and the 10 sites of SNPs which are GIRK3 subunit gene polymorphisms shown in Table 8 among the GIRK channel gene polymorphisms in Japanese healthy subjects, a haplotype is estimated using Haplotype Estimation. The estimated haplotypes are shown in Tables 9 and 10.

TABLE 9

| Gene name: GIRK2 | | Gene polymorphism name | | | | | | | |
|---|---|---|---|---|---|---|---|---|---|
| | | | | | | IVS1 | | | |
| Haplotype No. | Frequency | G-1250A | T-244C | C-227T | A-68G | C75167T | A1032G | C1569T | C1843G |
| 1 | 33.42% | A | C | T | G | T | G | T | C |
| 2 | 15.54% | G | T | C | G | T | G | T | C |
| 3 | 11.58% | A | C | T | G | T | A | T | C |
| 4 | 7.02% | G | T | C | A | T | G | T | C |
| 5 | 6.12% | A | C | T | G | C | A | T | C |
| 6 | 5.70% | G | T | C | G | T | A | T | C |
| 7 | 5.13% | A | C | T | G | C | G | T | C |
| 8 | 3.48% | G | T | C | G | C | G | T | C |
| 9 | 3.12% | A | C | T | G | T | A | C | C |
| 10 | 5 or more haplotypes which are estimated to occur at a frequency of less than 3% | | | | | | | | |
| Total | 100.00% | | | | | | | | |

TABLE 10

| Gene name: GIRK3 | | Gene polymorphism name | | | | | | | | | |
|---|---|---|---|---|---|---|---|---|---|---|---|
| Haplotype No. | Frequency | A-1329C | C-979G | C-968G | A-447G | C1211T | C1339T | C1781T | C1817T | G2069A | C2429T |
| 1 | 51.53% | A | C | G | G | C | C | C | C | G | C |
| 2 | 19.57% | A | C | G | G | C | C | T | T | G | C |
| 3 | 11.31% | A | C | C | A | C | T | T | C | A | T |
| 4 | 6.08% | A | C | C | A | C | C | C | C | G | C |

TABLE 10-continued

| Gene name: GIRK3 | | Gene polymorphism name | | | | | | | | | |
|---|---|---|---|---|---|---|---|---|---|---|---|
| Haplotype No. | Frequency | A-1329C | C-979G | C-968G | A-447G | C1211T | C1339T | C1781T | C1817T | G2069A | C2429T |
| 5 | 6.08% | A | C | G | G | C | T | T | C | A | T |
| 6 | 2.17% | A | C | G | G | C | T | T | T | G | C |
| 7 | 1.09% | A | G | C | A | C | T | T | C | A | T |
| 8 | 1.09% | C | C | C | A | C | T | T | C | A | T |
| 9 | 1.09% | A | C | G | G | T | T | T | C | A | T |
| Total | 100.01% | | | | | | | | | | |

As shown in Table 9, at least 14 haplotypes were estimated as the haplotype of GIRK2 subunit gene polymorphism in the Japanese healthy subjects, and among these, there were 9 haplotypes observed at a high frequency of 3% or higher (haplotype No. 1 to No. 9). Incidentally, 5 or more haplotypes which are estimated to occur at a frequency of less than 3% are collectively shown in haplotype No. 10 in Table 9.

Further, as shown in Table 10, 9 haplotypes were estimated as the haplotype of GIRK3 subunit gene polymorphism in the Japanese healthy subjects, and among these, there were 5 haplotypes observed at a high frequency of 3% or higher (haplotype No. 1 to No. 5).

Based on the haplotype frequencies of the haplotype analysis shown in Tables 9 and 10, a linkage disequilibrium analysis was carried out. The results are shown in Tables 11 and 12. The linkage disequilibrium among the GIRK2 subunit gene polymorphisms in the Japanese healthy subjects is shown in Table 11, and the linkage disequilibrium among the GIRK3 subunit gene polymorphisms in the Japanese healthy subjects is shown in Table 12.

TABLE 11

| | Gene name: GIRK2 Gene polymorphism name | | | | | D' | | | | |
|---|---|---|---|---|---|---|---|---|---|---|
| | | A-1361G | G-1250A | T-244C | C-227T | A-68G | IVS1 C75167T | A1032G | C1569T | C1843G |
| $r^2$ | A-1361G | | 1.000 | 1.000 | 1.000 | — | 1.000 | 1.000 | 1.000 | 1.000 |
| | G-1250A | 0.017 | | 1.000 | 1.000 | 1.000 | 0.136 | 0.037 | 0.518 | 0.159 |
| | T-244C | 0.017 | 1.000 | | 1.000 | 1.000 | 0.114 | 0.020 | 0.505 | 0.104 |
| | C-227T | 0.017 | 1.000 | 1.000 | | 1.000 | 0.114 | 0.020 | 0.505 | 0.104 |
| | A-68G | — | 0.153 | 0.153 | 0.153 | | 0.191 | 0.398 | 0.152 | 0.093 |
| | IVS1C75167T | 0.002 | 0.007 | 0.005 | 0.005 | 0.014 | | 0.078 | 1.000 | 0.044 |
| | A1032G | 0.020 | 0.000 | 0.000 | 0.000 | 0.034 | 0.003 | | 0.603 | 0.401 |
| | C1569T | 0.001 | 0.029 | 0.028 | 0.028 | 0.000 | 0.015 | 0.046 | | 0.091 |
| | C1843G | 0.192 | 0.002 | 0.001 | 0.001 | 0.004 | 0.000 | 0.017 | 0.007 | |

TABLE 12

| | Gene name: GIRK3 Gene Polymorphism name | | | | | D' | | | | |
|---|---|---|---|---|---|---|---|---|---|---|
| | | A-1329C | C-979G | C-968G | A-447G | C1211T | C1339T | C1781T | C1817T | G2069A | C2429T |
| $r^2$ | A-1329C | | 1.000 | 1.000 | 1.000 | 1.000 | 1.000 | 1.000 | 1.000 | 1.000 | 1.000 |
| | C-979G | 0.000 | | 1.000 | 1.000 | 1.000 | 1.000 | 1.000 | 1.000 | 1.000 | 1.000 |
| | C-968G | 0.042 | 0.042 | | 1.000 | 1.000 | 0.614 | 0.483 | 1.000 | 0.637 | 0.637 |
| | A-447G | 0.042 | 0.042 | 1.000 | | 1.000 | 0.607 | 0.491 | 1.000 | 0.629 | 0.629 |
| | C1211T | 0.000 | 0.000 | 0.003 | 0.003 | | 1.000 | 1.000 | 1.000 | 1.000 | 1.000 |
| | C1339T | 0.032 | 0.032 | 0.312 | 0.288 | 0.032 | | 1.000 | 1.000 | 1.000 | 1.000 |
| | C1781T | 0.014 | 0.014 | 0.080 | 0.079 | 0.014 | 0.429 | | 1.000 | 1.000 | 1.000 |
| | C1817T | 0.003 | 0.003 | 0.068 | 0.068 | 0.040 | 0.088 | 0.338 | | 1.000 | 1.000 |
| | G2069A | 0.035 | 0.035 | 0.380 | 0.349 | 0.035 | 0.892 | 0.382 | 0.078 | | 1.000 |
| | C2429T | 0.035 | 0.035 | 0.380 | 0.349 | 0.035 | 0.892 | 0.382 | 0.078 | 1.000 | |

A linkage disequilibrium block was estimated from the results of the linkage disequilibrium analysis (Tables 11 and 12) using Haploview (which is accessible from www.broad.mit.edu/mpg/haploview/index.php).

In Table 11, when the gene polymorphisms are named sequentially from the top or the left such that A-1361G is named "SNP1", G-1250A is named "SNP2" . . . , and C1843 is named "SNP9", a D' value, which is an index of a linkage disequilibrium between SNP1 and SNP2, is calculated and the resulting value is written in the cell at the intersection of the row of SNP1 and the column of SNP2 (upper right side of the table). Further, an $r^2$ value, which is a more stringent index of the linkage disequilibrium, is calculated in the same manner, and the resulting value is written in the cell at the intersection of the column of SNP1 and the row of SNP2 (lower left side of the table). Further, as a result of linkage disequilibrium analysis, with regard to a combination of gene polymorphisms showing a complete linkage disequilibrium (D'=1), the numerical value is underlined, and with regard to a combination showing an absolute linkage disequilibrium (D'=1, $r^2$=1), the value is represented by a bold and italic form. Also, the same shall apply to Table 12.

When focusing attention on the D' values in Table 11, a complete linkage disequilibrium was observed in many combinations of gene polymorphisms centering on the 5' flanking region. Further, when focusing attention on the $r^2$ values, it was found that three gene polymorphisms in the 5' flanking region showed a strong linkage disequilibrium (absolute linkage disequilibrium). G-1250A was found to be suitable as a Tag SNP representing this linkage disequilibrium block.

Further, when focusing attention on the D' values in Table 12, a complete linkage disequilibrium was observed in many combinations of gene polymorphisms. Further, when focusing attention on the $r^2$ values, it was found that two gene polymorphisms in each of the 5' flanking region and 3' noncoding region of exon 3 showed a strong linkage disequilibrium.

Further, a linkage disequilibrium block was estimated from the results of the linkage disequilibrium analysis (Tables 11 and 12) using Haploview (which is accessible from www.broad.mit.edu/mpg/haploview/index.php). As a result, with regard to SNP in the GIRK2 subunit gene shown in Table 11, one linkage disequilibrium block containing G-1250A as a Tag SNP was confirmed. In a similar manner, with regard to SNP in the GIRK3 subunit gene shown in Table 12, a total of two linkage disequilibrium blocks were confirmed in the 5' flanking region and 3' noncoding region of exon 3.

Example 2

Correlation Between GIRK2 Subunit Gene Polymorphism (A1032G) and Required Number of Administration of Analgesics and Total Amount of Analgesics A correlation between the GIRK channel gene polymorphism and the required number of administration of analgesics was examined. Genomic DNA was extracted from the blood or the oral mucosa of 123 patients undergoing surgery, and one gene polymorphism (A1032G) in the GIRK2 subunit gene was determined. Then, a correlation between these results of determination of the gene polymorphism and the required number of administration of analgesics and the total amount of analgesics was analyzed.

Incidentally, as the analgesic, analgesics such as pentazocine and pethidine, which are mainly administered intravenously, buprenorphine, diclofenac and indomethacin, which are mainly administered as a suppository, flurbiprofen axetil, which is injected by intravenous infusion, as well as epidural morphine and marcain were used.

Incidentally, the total amount of analgesics in terms of pentazocine means the total amount of analgesics (mg) in the case where the amount of each administered analgesic is converted to a value corresponding to the potency equivalent to pentazocine. The conversion of the amount of each analgesic to a value corresponding to the potency of pentazocine was carried out by setting a potency equivalent to pentazocine to 35 mg in the case of pethidine (Opystan), 0.4 mg in the case of buprenorphine (Lepetan), mg in the case of diclofenac (Voltaren), 100 mg in the case of flurbiprofen axetil (Ropion), 2 mg in the case of epidural morphine, and 20 ml in the case of marcain (0.5%).

Figure 3:
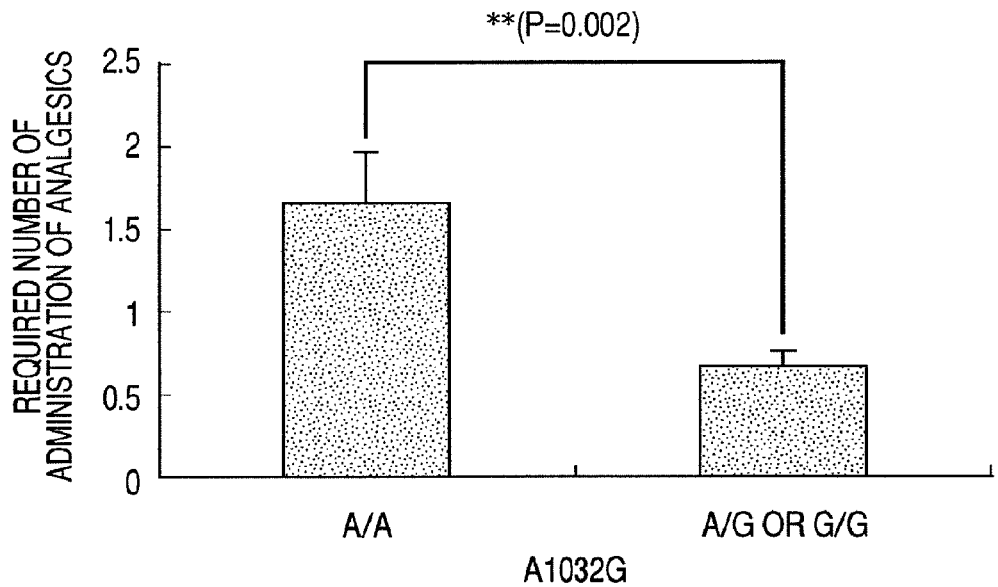
FIG. 3 is a graph showing an effect of GIRK2 subunit gene polymorphism (A1032G) on the required number of administration in 24 hours after surgery in patients administered with analgesics in surgery (average of males and females±standard error)

As a result, as shown in the following Table 13 and FIG. 3, in a group of patients who did not have a major allele (G) of the gene polymorphism (A1032G), the required number of administration of analgesics was significantly higher compared with a group of patients who had the allele G. Moreover, these results were almost the same between males and females (male: M, female: F).

TABLE 13

Effect of GIRK2 A1032G polymorphism on required number of administration in 24 hours after surgery in patients administered with analgesics in surgery (descriptive statistics by gender)

| GIRK2 A1032G | Gender | Average ※ | Standard deviation | Number of test subjects (subjects) |
|---|---|---|---|---|
| A/A | F | 1.67 | 2.251 | 6 |
|  | M | 1.40 | 1.140 | 5 |
|  | Total | 1.55 | 1.753 | 11 |
| A/G or G/G | F | 0.66 | 0.915 | 47 |
|  | M | 0.71 | 0.931 | 65 |
|  | Total | 0.69 | 0.921 | 112 |
| Total | F | 0.77 | 1.154 | 53 |
|  | M | 0.76 | 0.955 | 70 |
|  | Total | 0.76 | 1.041 | 123 |

※ Required number of administration of analgesics in 24 hours after surgery (number)

Figure 4:
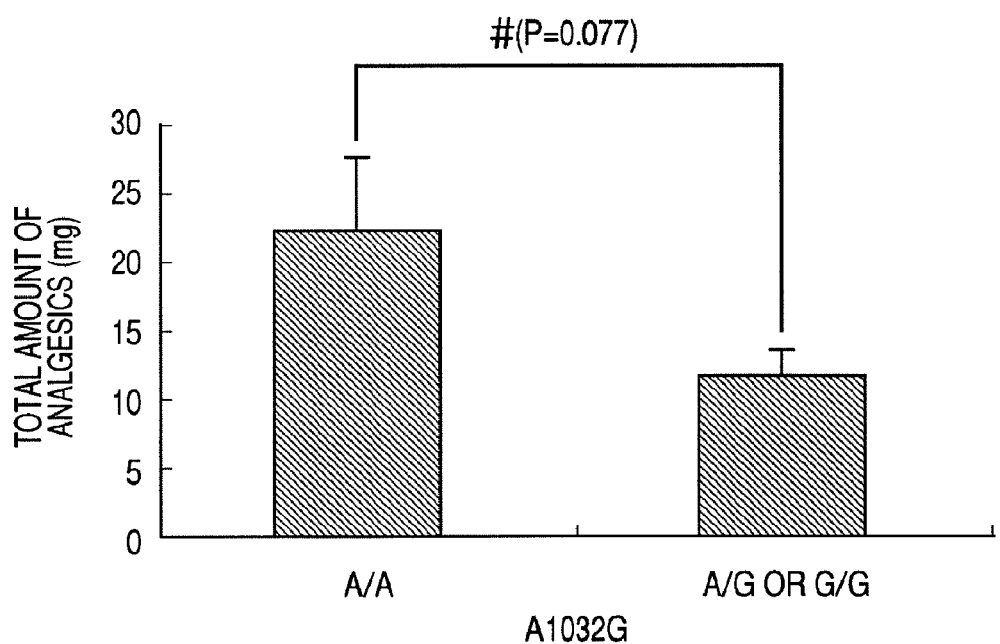
FIG. 4 is a graph showing an effect of GIRK2 subunit gene polymorphism (A1032G) on the total amount of analgesics in terms of pentazocine in patients administered with analgesics in surgery (average of males and females±standard error)

Further, a correlation between the GIRK channel gene polymorphism and the total amount of analgesics was examined. As a result, as shown in the following Table and FIG. 4, a tendency that the total amount of analgesics was statistically larger in a group of patients who did not have a major allele (G) of the gene polymorphism (A1032G) compared with a group of patients who had the allele G was observed. In particular, the total amount thereof was statistically significantly large in females (P=0.033).

TABLE 14

Effect of GIRK2 A1032G polymorphism on total amount of analgesics in terms of pentazocine in patients administered with analgesics in surgery (descriptive statistics by gender)

| GIRK2 A1032G | Gender | Average ※ | Standard deviation | Number of test subjects (subjects) |
|---|---|---|---|---|
| A/A | F | 23.75 | 40.366 | 6 |
|  | M | 16.50 | 17.103 | 5 |
|  | Total | 20.45 | 30.757 | 11 |
| A/G or G/G | F | 9.73 | 13.715 | 47 |
|  | M | 13.50 | 18.759 | 65 |
|  | Total | 11.92 | 16.863 | 112 |
| Total | F | 11.32 | 18.525 | 53 |
|  | M | 13.71 | 18.547 | 70 |
|  | Total | 12.68 | 18.499 | 123 |

※ Total amount of analgesics in terms of pentazocine (mg)

From the above results, it is considered that in individuals who did not have a major allele (G) of the GIRK2 subunit gene polymorphism (A1032G), the sensitivity to analgesics was low and the required number of administration of analgesics was high and the total amount of analgesics was large. Accordingly, it was shown that by determining the GIRK channel gene polymorphism, the required number of administration of analgesics and the total amount of analgesics could be easily predicted.

Example 3

Correlation Between GIRK2 Subunit Gene Polymorphisms (A1032G and G-1250A) and Required Number of Administration of Analgesics and Total Amount of Analgesics A correlation between the GIRK2 subunit gene polymorphism and the required number of administration of analgesics was examined. A correlation between the GIRK2 subunit gene polymorphism and the required number of administration of analgesics and the total amount of analgesics after surgery in the case where the determination results of gene polymorphism (G-1250A) which is a Tag SNP representing the linkage disequilibrium block in the 5' flanking region of the GIRK2 subunit gene to the above-mentioned determination results of the GIRK2 subunit gene polymorphism (A1032G) was analyzed. Incidentally, the data to be analyzed was the same as in Example 2.

Figure 5:
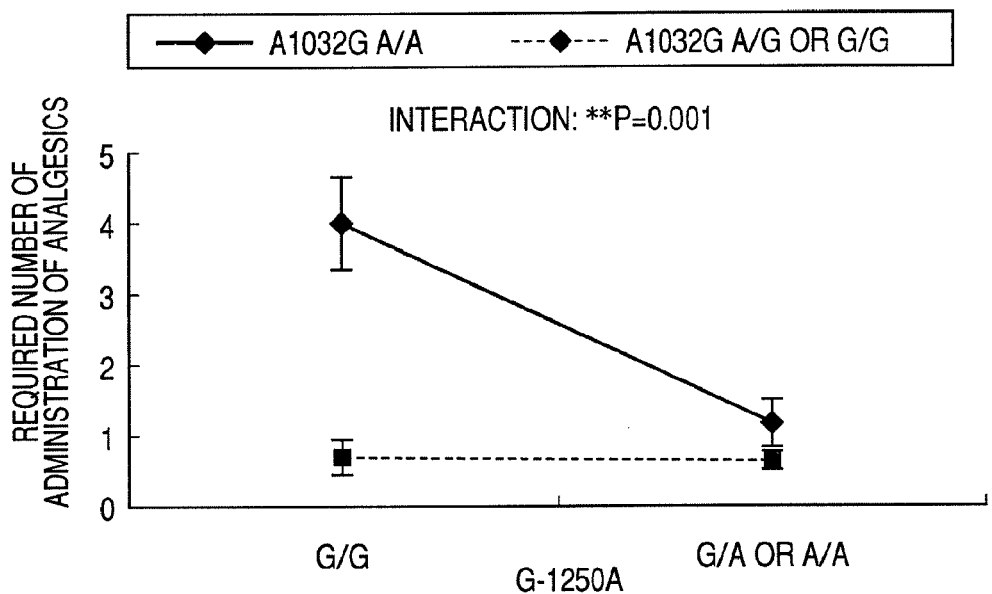
FIG. 5 is a graph showing an effect of GIRK2 subunit gene polymorphisms (A1032G and G-1250A) on the required number of administration in 24 hours after surgery in patients administered with analgesics in surgery.

As a result of the analysis, as shown in the following Table 15 and FIG. 5, with regard to the required number of administration of analgesics, the presence or absence of a major allele (G) of the gene polymorphism (A1032G) and the presence or absence of a major allele (A) of the gene polymorphism (G-1250A) showed a significant interaction.

That is, in a group of patients who did not have both major alleles of the GIRK2 subunit gene polymorphisms (A1032G and G-1250A), the required number of administration of analgesics was significantly higher compared with a group of patients who had either one of the major alleles or a group of patients who had both major alleles.

TABLE 15

Interaction of GIRK2 A1032G polymorphism and GIRK2 G-1250A polymorphism with respect to required number of administration in 24 hours after surgery in patients administered with analgesics in surgery

| GIRK2<br>G-1250A | GIRK2<br>A1032G | Average<br>※ | Standard<br>deviation | Number of<br>test subjects<br>(subjects) |
|---|---|---|---|---|
| G/G | A/A | 4.00 | 2.828 | 2 |
|  | A/G or G/G | 0.69 | 0.946 | 16 |
|  | Total | 1.06 | 1.552 | 18 |
| G/A or A/A | A/A | 1.00 | 1.069 | 8 |
|  | A/G or G/G | 0.66 | 0.893 | 92 |
|  | Total | 0.69 | 0.907 | 100 |
| Total | A/A | 1.60 | 1.838 | 10 |
|  | A/G or G/G | 0.67 | 0.897 | 108 |
|  | Total | 0.75 | 1.031 | 118 |

※ Required number of administration of analgesics in 24 hours after surgery (frequency)

Figure 6:
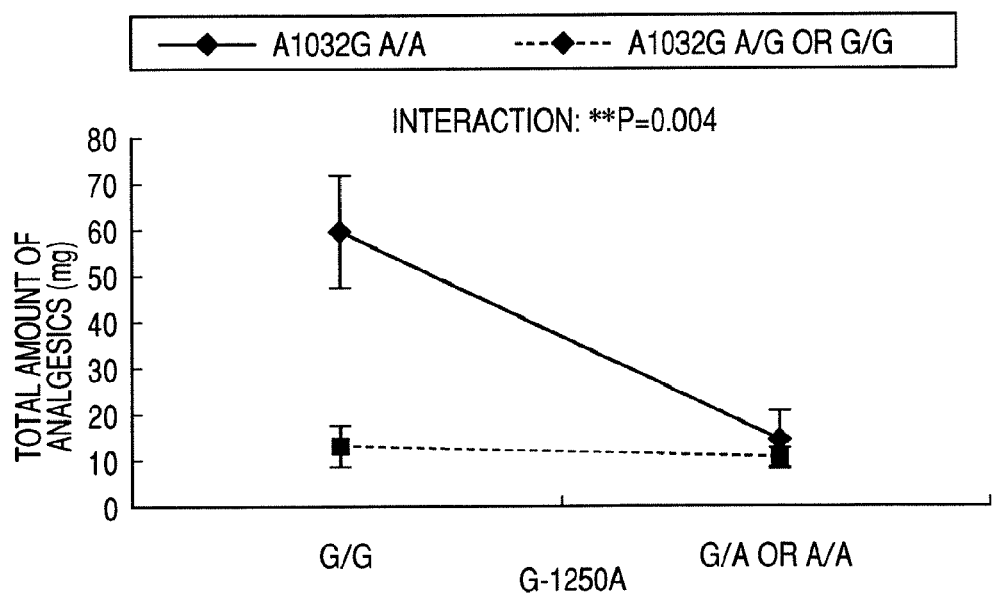
FIG. 6 is a graph showing an effect of GIRK2 subunit gene polymorphisms (A1032G and G-1250A) on the total amount of analgesics in terms of pentazocine in patients administered with analgesics in surgery.

Further, a correlation between the GIRK2 subunit gene polymorphisms (A1032G and G-1250A) and the total amount of analgesics was examined. As a result, with regard also to the total amount of analgesics, as shown in the following Table 16 and FIG. 6, the presence or absence of the allele G of the gene polymorphism (A1032G) and the presence or absence of the allele A of the gene polymorphism (G-1250A) showed a significant interaction.

That is, in a group of patients who did not have both major alleles of the GIRK2 subunit gene polymorphisms (A1032G and G-1250A), the total amount of analgesics was significantly larger compared with a group of patients who had either one of the major alleles or a group of patients who had both major alleles.

TABLE 16

Interaction of GIRK2 A1032G polymorphism and GIRK2 G-1250A polymorphism with respect to total amount of analgesics in terms of pentazocine in patients administered with analgesics in surgery

| GIRK2<br>G-1250A | GIRK2<br>A1032G | Average<br>※ | Standard<br>deviation | Number of<br>test subjects<br>(subjects) |
|---|---|---|---|---|
| G/G | A/A | 60.00 | 63.640 | 2 |
|  | A/G or G/G | 13.59 | 18.618 | 16 |
|  | Total | 18.75 | 27.736 | 18 |
| G/A or A/A | A/A | 12.19 | 14.966 | 8 |
|  | A/G or G/G | 11.25 | 16.093 | 92 |
|  | Total | 11.32 | 15.936 | 100 |
| Total | A/A | 21.75 | 32.103 | 10 |
|  | A/G or G/G | 11.60 | 16.418 | 108 |
|  | Total | 12.46 | 18.272 | 118 |

※ Total amount of analgesics in terms of pentazocine (mg)

From the above results, it was shown that by determining the gene polymorphism (G-1250A) which is a Tag SNP representing the linkage disequilibrium block in the 5' flanking region of the GIRK2 subunit gene to the gene polymorphism (A1032G) in the GIRK2 subunit gene, the required number of administration of analgesics and the total amount of analgesics could be more easily predicted. That is, it was found that the required number of administration of analgesics and the total amount of analgesics could be easily predicted from the determination results of plural gene polymorphisms in the GIRK channel gene.

Example 4

Correlation Between GIRK3 Subunit Gene Polymorphism and Sensitivity to Methamphetamine In order to examine a correlation between the GIRK channel gene polymorphism and drug sensitivity associated with vulnerability to drug dependence, genomic DNA was extracted from the blood of 197 methamphetamine-dependent patients and 360 healthy subjects, and the GIRK3 subunit gene polymorphism (C1339T) was determined. The results are shown in the following Table 17.

As is evident from Table 17, it was shown that the minor allele (T) frequency of the gene polymorphism (C1339T) which is a nonsynonymous substitution was significantly high in the methamphetamine-dependent patients compared with the healthy subjects. Thus, a significant frequency difference in both the genotype frequency and allele frequency was observed.

TABLE 17

Comparison of genotype and allele frequencies of GIRK3 C1339T polymorphism in healthy subjects and methamphetamine-dependent patients
Gene polymorphism name: GIRK3 C1339T

| Sample name | (Number of samples) | Genotype frequency (%) | | | | Allele frequency | | |
|---|---|---|---|---|---|---|---|---|
| | | C/C | C/T | T/T | | C | T | |
| Healthy subjects | (360) | 207 (57.5%) | 133 (36.9%) | 20 (5.6%) | * (P = 0.034) | 0.760 | 0.240 | * (P = 0.017) |
| Methamphetamine-dependent patients | (208) | 104 (50.0%) | 81 (38.9%) | 23 (11.1%) | | 0.695 | 0.305 | |

Further, in order to examine a correlation between the GIRK channel gene polymorphism and drug sensitivity associated with prolongation of stimulant-induced psychosis, a group of patients with prolonged stimulant-induced psychosis (for one month or more) and a group of healthy subjects were compared. The results are shown in the following Table 18. Here, the methamphetamine-dependent patients were classified into two groups: a group of early disappearance type in which the period of duration of delusion or hallucination was less than one month; and a group of prolonged and continuous type in which the period of duration of delusion or hallucination was one month or more.

As is evident from Table 18, with regard to the gene polymorphism (C1339T), a significant frequency difference in both genotype frequency and allele frequency was observed.

The entire disclosure of each and every foreign patent application from which the benefit of foreign priority has been claimed in the present application is incorporated herein by reference, as if fully set forth.

SEQUENCE LISTING FREE TEXT

SEQ ID NO: 1: An oligonucleotide containing a gene polymorphism (A-1361G) in GIRK2 subunit gene. r in the nucleotide sequence indicates the gene polymorphism (A-1361G).

SEQ ID NO: 2: An oligonucleotide containing a gene polymorphism (G-1250A) in GIRK2 subunit gene. r in the nucleotide sequence indicates the gene polymorphism (G-1250A).

TABLE 18

Comparison of genotype and allele frequencies of GIRK3 C1339T polymorphism in healthy subjects and methamphetamine-dependent patients classified based on period of duration of delusion or hallucination
Gene polymorphism name: GIRK3 C1339T

| Sample name | (Number of samples) | Genotype frequency (%) | | | | Allele frequency | | |
|---|---|---|---|---|---|---|---|---|
| | | C/C | C/T | T/T | | C | T | |
| Healthy subjects | (360) | 207 (57.5%) | 133 (36.9%) | 20 (5.6%) | * (P = 0.012) | 0.760 | 0.240 | * (P = 0.036) |
| Methamphetamine-dependent patients | Period of duration of delusion or hallucination | | | | | | | |
| | Early disappearance type (100) | 53 (53.0%) | 41 (41.0%) | 6 (6.0%) | | 0.735 | 0.265 | |
| | Prolonged and continuous type (71) | 36 (50.7%) | 24 (33.8%) | 11 (15.5%) | | 0.676 | 0.324 | |

From the above results, it was shown that by determining the genotype frequency and the allele frequency of the GIRK channel gene polymorphism, vulnerability to drug dependence and drug sensitivity associated with prolongation of stimulant-induced psychosis could be easily predicted.

According to the present invention, a GIRK channel gene polymorphism capable of evaluating an individual difference associated with drug sensitivity or disease vulnerability, a method of evaluating drug sensitivity or disease vulnerability using the gene polymorphism and the like can be provided. By this evaluation method, a proper prescribed amount, a proper prescribed schedule associated with a narcotic drug such as morphine and the like can be easily found, and hence the method is extremely useful for personalized pain therapy, drug dependence therapy and the like.

SEQ ID NO: 3: An oligonucleotide containing a gene polymorphism (T-244C) in GIRK2 subunit gene. y in the nucleotide sequence indicates the gene polymorphism (T-244C)

SEQ ID NO: 4: An oligonucleotide containing a gene polymorphism (C-227T) in GIRK2 subunit gene. y in the nucleotide sequence indicates the gene polymorphism (C-227T).

SEQ ID NO: 5: An oligonucleotide containing a gene polymorphism (A-68G) in GIRK2 subunit gene. r in the nucleotide sequence indicates the gene polymorphism (A-68G).

SEQ ID NO: 6: An oligonucleotide containing a gene polymorphism (IVS1C75167T) in GIRK2 subunit gene. y in the nucleotide sequence indicates the gene polymorphism (IVS1C75167T).

SEQ ID NO: 7: An oligonucleotide containing a gene polymorphism (A1032G) in GIRK2 subunit gene. r in the nucleotide sequence indicates the gene polymorphism (A1032G).

SEQ ID NO: 8: An oligonucleotide containing a gene polymorphism (C1569T) in GIRK2 subunit gene. y in the nucleotide sequence indicates the gene polymorphism (C1569T).

SEQ ID NO: 9: An oligonucleotide containing a gene polymorphism (C1843G) in GIRK2 subunit gene. s in the nucleotide sequence indicates the gene polymorphism (C1843G).

SEQ ID NO: 10: An oligonucleotide containing a gene polymorphism (A-1329C) in GIRK3 subunit gene. m in the nucleotide sequence indicates the gene polymorphism (A-1329C).

SEQ ID NO: 11: An oligonucleotide containing a gene polymorphism (C-979G) in GIRK3 subunit gene. s in the nucleotide sequence indicates the gene polymorphism (C-979G).

SEQ ID NO: 12: An oligonucleotide containing a gene polymorphism (C-968G) in GIRK3 subunit gene. s in the nucleotide sequence indicates the gene polymorphism (C-968G).

SEQ ID NO: 13: An oligonucleotide containing a gene polymorphism (A-447G) in GIRK3 subunit gene. r in the nucleotide sequence indicates the gene polymorphism (A-447G).

SEQ ID NO: 14: An oligonucleotide containing a gene polymorphism (C1211T) in GIRK3 subunit gene. y in the nucleotide sequence indicates the gene polymorphism (C1211T).

SEQ ID NO: 15: An oligonucleotide containing a gene polymorphism (C1339T) in GIRK3 subunit gene. y in the nucleotide sequence indicates the gene polymorphism (C1339T)

SEQ ID NO: 16: an Oligonucleotide Containing a Gene polymorphism (C1781T) in GIRK3 subunit gene. y in the nucleotide sequence indicates the gene polymorphism (C1781T).

SEQ ID NO: 17: An oligonucleotide containing a gene polymorphism (C1817T) in GIRK3 subunit gene. y in the nucleotide sequence indicates the gene polymorphism (C1817T).

SEQ ID NO: 18: An oligonucleotide containing a gene polymorphism (G2069A) in GIRK3 subunit gene. r in the nucleotide sequence indicates the gene polymorphism (G2069A).

SEQ ID NO: 19: An oligonucleotide containing a gene polymorphism (C2429T) in GIRK3 subunit gene. y in the nucleotide sequence indicates the gene polymorphism (C2429T).

SEQ ID NO: 20: A nucleotide sequence of a primer for detecting a gene polymorphism (G-1250A) in GIRK2 subunit gene.

SEQ ID NO: 21: A nucleotide sequence of a primer for detecting a gene polymorphism (G-1250A) in GIRK2 subunit gene.

SEQ ID NO: 22: A nucleotide sequence of a primer for detecting a gene polymorphism (A1032G) in GIRK2 subunit gene.

SEQ ID NO: 23: A nucleotide sequence of a primer for detecting a gene polymorphism (A1032G) in GIRK2 subunit gene.

SEQ ID NO: 24: A nucleotide sequence of a primer for detecting a gene polymorphism (C1339T) in GIRK3 subunit gene.

SEQ ID NO: 25: A nucleotide sequence of a primer for detecting a gene polymorphism (C1339T) in GIRK3 subunit gene.

What is claimed is:

1. A method of determining if a human subject has an increased need for a narcotic analgesic to mitigate pain, which method comprises:
detecting a GIRK2 polymorphism in a nucleic acid sample from a human subject, wherein the GIRK2 polymorphism is an A to G polymorphism at position 1032 of the GIRK2 gene and is at position 51 with respect to SEQ ID NO: 7, and determining the human subject's genotype at position 1032 of the GIRK2 gene, wherein detection of an A/A genotype at position 1032 of the GIRK2 gene indicates that the human subject has an increased need for a narcotic analgesic to mitigate pain in comparison to human subjects having an A/G or G/G genotype at position 1032.

2. The method according to claim 1, wherein the method further comprises analyzing the nucleic acid sample for the presence of a second polymorphism in the GIRK2 gene, wherein the second polymorphism is a G to A polymorphism at position 1250 of the GIRK2 gene and is at position 51 with respect to SEQ ID NO: 2.

3. The method according to claim 1, wherein said pain is due to surgery.

4. The method according to claim 1, wherein said human subject is a female human subject.

5. The method of determining if a human subject has an increased need for a narcotic analgesic to mitigate pain according to claim 1, wherein the narcotic analgesic is pentazocine.

6. A method of determining a dosage amount of a narcotic analgesic or a number of dosages of a narcotic analgesic to be administered to a human subject, which method comprises:
detecting whether a GIRK2 polymorphism is present in a nucleic acid sample from a human subject, wherein the GIRK2 polymorphism is an A to G polymorphism at position 1032 of the GIRK2 gene and is at position 51 with respect to SEQ ID NO: 7, and determining the human subject's genotype at position 1032 of the GIRK2 gene, wherein detection of an A/A genotype at position 1032 in the GIRK2 gene indicates that an increase in the dosage amount of the narcotic analgesic or an increase in the number of dosages of the narcotic analgesic are to be administered to said human subject in comparison to a human subject having an A/G or G/G genotype at position 1032.

7. The method according to claim 6, wherein the method further comprises analyzing the nucleic acid sample for the presence of a second polymorphism in the GIRK2 gene, wherein the second polymorphism is a G to A polymorphism at position 1250 of the GIRK2 gene and is at position 51 with respect to SEQ ID NO: 2.

8. The method according to claim 6, wherein the narcotic analgesic mitigates pain due to surgery.

9. The method according to claim 6, wherein said human subject is a female human subject.

10. The method of according to claim 6, wherein said narcotic analgesic is pentazocine.

11. The method according to claim 6, wherein the narcotic analgesics are to be administered 24 hours after surgery.

12. The method according to claim 1, wherein the narcotic analgesic is selected from the group consisting of morphine, DAMGO, codeine, methadone, carfentanil, fentanyl, heroin, nalozone, naltrexone, nalorphine, levallorphan, pentazocine, pethidine, buprenorphine, oxycodone, hydrocodone, levorphanol, etorphine, dihydroetorphine, hydromorphone, oxymorphone, and tramadol.

13. The method according to claim 6, wherein the narcotic analgesic is selected from the group consisting of morphine, DAMGO, codeine, methadone, carfentanil, fentanyl, heroin, nalozone, naltrexone, nalorphine, levallorphan, pentazocine, pethidine, buprenorphine, oxycodone, hydrocodone, levorphanol, etorphine, dihydroetorphine, hydromorphone, oxymorphone, and tramadol.

14. The method according to claim 12, wherein the narcotic analgesic is selected from the group consisting of morphine, pentazocine, buprenorphine, pethidine, fentanyl, diclofenac, flurbiprofen, and indomethacin.

15. The method according to claim 13, wherein said narcotic analgesic is selected from the group consisting of morphine, pentazocine, buprenorphine, pethidine, fentanyl, diclofenac, flurbiprofen, and indomethacin.

* * * * *